(12) United States Patent
Baker et al.

(10) Patent No.: US 8,747,872 B2
(45) Date of Patent: Jun. 10, 2014

(54) NANOEMULSION THERAPEUTIC COMPOSITIONS AND METHODS OF USING THE SAME

(75) Inventors: James R. Baker, Ann Arbor, MI (US); Sivaprakash Rathinavelu, Naperville, IL (US); Paul E. Makidon, Webberville, MI (US); John J. LiPuma, Ann Arbor, MI (US); Shraddha Nigavekar, Franklin, TN (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1207 days.

(21) Appl. No.: 12/114,573

(22) Filed: May 2, 2008

(65) Prior Publication Data

US 2008/0317799 A1 Dec. 25, 2008

Related U.S. Application Data

(60) Provisional application No. 60/927,309, filed on May 2, 2007.

(51) Int. Cl.
| | | |
|---|---|---|
| *A01N 25/00* | (2006.01) | |
| *A61K 9/00* | (2006.01) | |
| *A01N 25/04* | (2006.01) | |
| *A61K 9/107* | (2006.01) | |
| *A61K 6/00* | (2006.01) | |

(52) U.S. Cl.
CPC .............. *A61K 9/0078* (2013.01); *A01N 25/04* (2013.01); *A61K 9/1075* (2013.01); *A61K 6/0008* (2013.01)
USPC ...................................................... 424/405

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,596,556 A | 6/1986 | Morrow | |
| 4,675,189 A | 6/1987 | Kent | |
| 4,895,452 A | 1/1990 | Yiournas | |
| 5,075,109 A | 12/1991 | Tice | |
| 5,103,497 A | 4/1992 | Hicks | |
| 5,133,974 A | 7/1992 | Paradissis | |
| 5,284,656 A | 2/1994 | Platz | |
| 5,407,686 A | 4/1995 | Patel | |
| 5,451,569 A | 9/1995 | Wong | |
| 5,510,104 A | 4/1996 | Allen | |
| 5,547,677 A | 8/1996 | Wright | |
| 5,549,901 A | 8/1996 | Wright | |
| 5,618,840 A | 4/1997 | Wright | |
| 5,700,679 A | 12/1997 | Wright | |
| 5,736,152 A | 4/1998 | Dunn | |
| 5,985,309 A | 11/1999 | Edwards | |
| 5,993,412 A | 11/1999 | Deily | |
| 5,997,848 A | 12/1999 | Patton | |
| 6,015,832 A | 1/2000 | Baker, Jr. et al. | |
| 6,051,256 A | 4/2000 | Platz | |
| RE37,053 E | 2/2001 | Hanes | |
| 6,294,204 B1 | 9/2001 | Rossling | |
| 6,423,344 B1 | 7/2002 | Platz | |
| 6,436,443 B2 | 8/2002 | Edwards | |
| 6,447,753 B2 | 9/2002 | Edwards | |
| 6,503,480 B1 | 1/2003 | Edwards | |
| 6,506,803 B1 | 1/2003 | Baker, Jr. et al. | |
| 6,518,239 B1 | 2/2003 | Kuo | |
| 6,559,189 B2 | 5/2003 | Baker, Jr. et al. | |
| 6,592,904 B2 | 7/2003 | Platz | |
| 6,635,283 B2 | 10/2003 | Edwards | |
| 6,635,676 B2 | 10/2003 | Baker, Jr. et al. | |
| 6,651,655 B1 | 11/2003 | Licalsi | |
| 7,767,216 B2 | 8/2010 | Baker, Jr. et al. | |
| 2002/0148463 A1* | 10/2002 | Strayer | 128/200.14 |
| 2003/0162251 A1* | 8/2003 | Feder et al. | 435/69.1 |
| 2004/0009245 A1* | 1/2004 | Vail et al. | 424/742 |
| 2005/0118270 A1* | 6/2005 | Moro et al. | 424/485 |
| 2005/0208083 A1 | 9/2005 | Annis | |
| 2005/0281843 A1 | 12/2005 | Singh | |
| 2006/0051385 A1* | 3/2006 | Scholz | 424/405 |
| 2006/0251684 A1 | 11/2006 | Annis | |
| 2007/0036831 A1 | 2/2007 | Baker, Jr. et al. | |

FOREIGN PATENT DOCUMENTS

| | | |
|---|---|---|
| CN | 1676125 A | 10/2005 |
| EP | 0517565 | 12/1992 |
| EP | 0904701 A2 | 3/1999 |
| WO | 97/48440 | 12/1997 |
| WO | 98/28037 | 7/1998 |
| WO | 99/27961 | 6/1999 |
| WO | WO2005/030172 A1 * | 4/2005 |

OTHER PUBLICATIONS

Adjei, et al., Bioavailability of leuprolide following intratracheal administration to beagle dogs, Int. J. Pharmaceutics 1990; 63:135-144.

Adjei, et al., Pulmonary Delivery of Peptide Drugs: Effect of Particle Size on Bioavailability of Leuprolide Acetate in Healthy Male Volunteers, Pharmaceutical Research 1990; 7:565-569.

Ampel, Emerging Disease Issues and Fungal Pathogens Associated with HIV Infection, Apr.-Jun. 1996, Emerg. Infect. Dis. 2(2): 109-116.

(Continued)

*Primary Examiner* — Bethany Barham
(74) *Attorney, Agent, or Firm* — Tyler J. Sisk; Casimir Jones, S.C.

(57) ABSTRACT

The present invention relates to methods and compositions for treating pulmonary infection. In particular, the present invention provides nanoemulsion compositions and methods of using the same to treat bacteria associated with biofilms (e.g., found in pulmonary infections). Compositions and methods of the present invention find use in, among other things, clinical (e.g. therapeutic and preventative medicine), industrial, and research applications.

23 Claims, 19 Drawing Sheets

(56) References Cited

OTHER PUBLICATIONS

Figure 1:
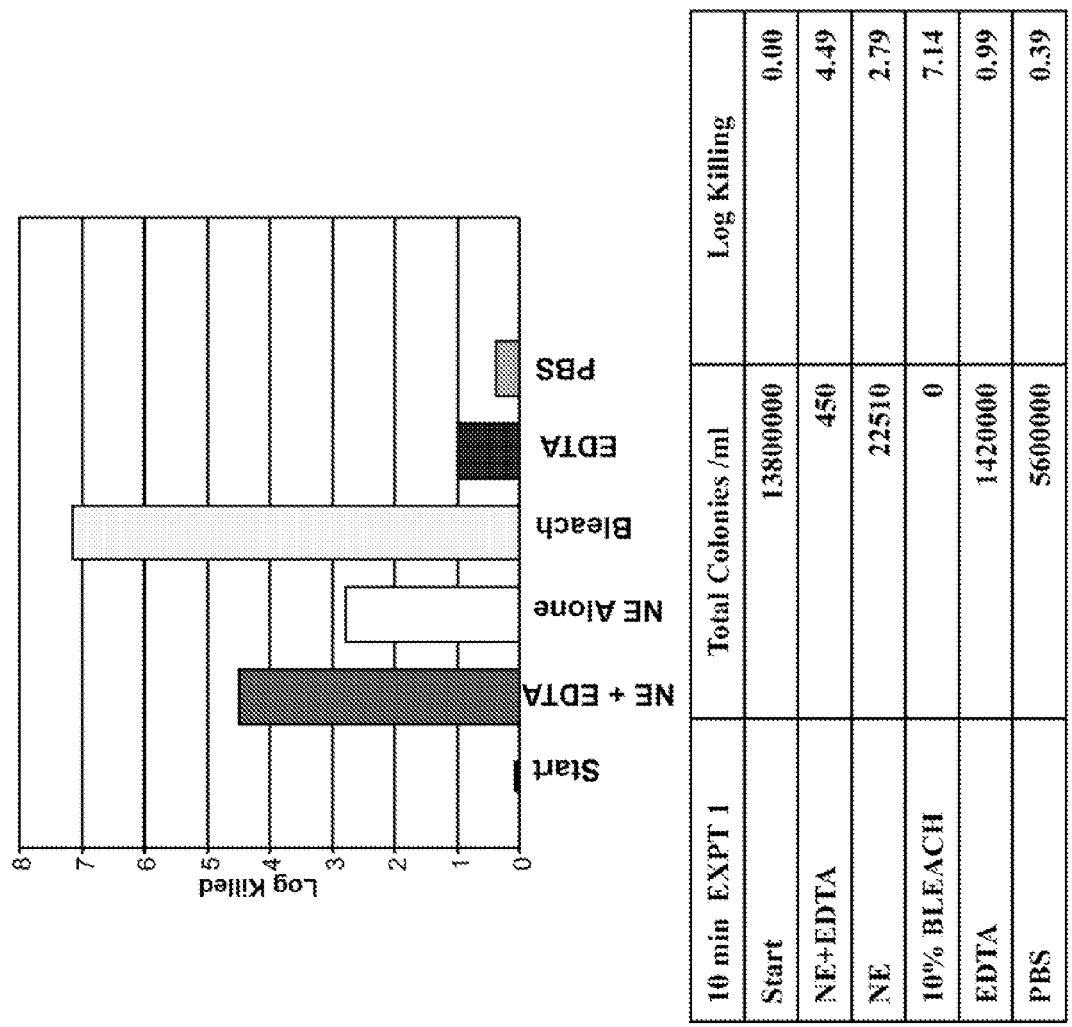

Applied Surfactants: Principles and Applications. Tharwat F. Tadros, Copyright 8 2005 Wiley-VCH Verlag GmbH & Co. KGaA, Weinheim ISBN: 3-527-30629-3 (book).
Biddick et al., Evidence of transmission of *Burkholderia cepacia, Burkholderia multivorans* and *Burkholderia dolosa* among persons with cystic fibrosis, FEMS Microbiol Lett 2003;228:57-62.
Braquet, et al., Effect of Endothelin-1 on Blood Pressure and Bronchopulmonary System of the Guinea Pig, J. Cardiovascular Pharmacology 1989 S143-S146.
Caraher et al., Comparison of antibiotic susceptibility of *Burkholderia cepacia* complex organisms when grown planktonically or as biofilm in vitro, Eur J Clin Microbiol Infect Dis. Mar. 2006;26(3):213-6.
Lambert, update: fatal and Severe Liver Injuries Associated with Rifampin and Pyrazinamide Treatment for Latent Tuberculosis Infection, CDC Morbidity and Mortality Weekly Report, Nov. 2002, 51(44): 998-999.
Chen et al., Endemicity and inter-city spread of *Burkholderia cepacia* genomovar III in cystic fibrosis, J Pediatr 2001;139:643-9.
Coenye and LiPuma, Multilocus Restriction Typing: A Novel Tool for Studying Global Epidemiology of *Burkholderia cepacia* Complex Infection in Cystic Fibrosis, J. Infect. Dis. 185:1454-1462.
Current Protocols in Microbiology (John Wiley & Sons, Inc., NJ, USA) (book).
Debs, et al., Lung-Specific Delivery of Cytokines Induces Sustained Pulmonary and Systemic Immunomodulation in Rats, J. Immunol. 1988; 140:3482-3488.
Desai et al., increasing resistance of planktonic and biofilm cultures of *Burkholderia cepacia* to ciprofloxacin and ceftazidime during exponential growth, J Antimicrob Chemother. Aug. 1998;42(2):153-60.
Dodds et al., Antifungal Pharmacodynamics: Review of the Literature and Clinical Applications, 2000 Pharmacotherapy 20(11): 1335-1355.
Dye et al., Global Burden of Tuberculosis—Estimated Incidence, prevalence, and Mortality by Country, 1999, JAMA 282: 677-686.
Eriksson et al., Virus validation of plasma-derived products produced by Pharmacia, with particular reference to immunoglobulins, Blood Coagulation and Fibtinolysis 5 (Suppl. 3):S37-S44 (1994).
Favre-Bonte et al., Detection of Pseudomonas aeruginosa cell-to-cell signals in lung tissue of cystic fibrosis patients, Microb Pathog. Mar. 2002;32(3):143-7.
Gerischer U (editor). (2008). Acinetobacter Molecular Biology, 1st ed., Caister Academic Press (book).
Goodman & Gilman's "The Pharmacological Basis of Therapeutics" Eds. Hardman et al., 9th Edition, Pub. McGraw Hill, chapters 43 through 50, 1996 (book).
Grebski et al., Effect of Physical and Chemical methods of Homogenization on Inflammatory Mediators in Sputum of Asthma Patients, Chest. May 2001;119(5):1521-5.
Hamouda and Baker, Antimicrobial mechanism of action of surfactant lipiid preparations in enteric Gram-negative bacilli, J Appl Microbiol. Sep. 2000;89(3):397-403.
Horowitz et al., Solvent/detergent-treated plasma: a virus-inactivated substitute for fresh frozen plasma, Blood 79:826 (1992).
Hubbard, et al., Anti-Neutrophil-Elastase Defenses of the Lower Respiratory Tract in α1-Antitrypsin Deficiencey Directly Augmented with an Aerosol of α1-Antitrypsin, (1989) Annals of Internal Medicine, vol. III, pp. 206-212.
Hunt et al., Macromolecular Mechanisms of Sputum Inhibition of Tobramycin Activity, Antimicrob Agents Chemother. Jan. 1995;39(1):34-9.
Ilium et al., Hyaluronic acid ester microspheres as a nasal deliverey system for insulin, J. Controlled Rel., 1994, 29:133-141.
Johnson et al., Linkage Analysis of Geographic and Clinical Clusters in *Pseudomonas cepacia* Infections by Multilocus Enzyme Electrophoresis and Ribotyping, J Clin Microbiol 1994;32:924-30.
Maha and Igarashi, The Effect of Nonionic Detergent on Dengue and Japanese Encephalitis Virus Antigens in Antigen Detection Elisa and IGM-Capture ELISA, Southeast Asian J. Trop. Med. Pub. Health 28:718 (1997).
Martin, Remington's Pharmaceutical Sciences, 15th Ed., Mack Publ. Co., Easton, Pa. (1975) (book).
McCutheon's vol. 1: Emulsions and Detergents—North American Edition, 2000 (book).
Merck Manual of Diagnosis and Therapy (17th ed., 1999) (book).
Moskowitz et al., Clinically Feasible Biofilm Susceptibility Assay for Isolates of *Pseudomonas aeruginosa* from Patients with Cystic Fibrosis, J Clin Microbiol. May 2004;42(5):1915-22.
McNabb et al., DNA Fingerprinting of *Mycobacterium tuberculosis*: Lessons Learned and Implications for the Future, 2002, Emerg. Infect. Dis. 8:11, pp. 1314-1319.
Oswein, et al. "Aerosolization of Proteins", 1990; Proceedings of Symposium on Respiratory Drug Delivery II Keystone, Colorado.
Portocala et al., Immunoelectrophoretic characterization of Sendai virus antigens, Virologie 27:261 (1976).
Rabinovich-Guilatt et al., Cationic Vectors in Ocular Drug Delivery, J Drug Target. 2004;12(9-10):623-33.
Rattan et al., Multidrug-Resistant *Mycobacterium tuberculosis*: Molecular Perspectives, 1998, Emerging Infectious Diseases, 4(2): 195-206.
Reik et al., Distribution of *Burkholderia cepacia* Complex Species among Isolates Recovered from Persons with or without Cystic Fibrosis, J Clin Microbiol. Jun. 2005;43(6):2926-8.
Navin et al., The Continued Threat of Tuberculosis, Emerging Infectious Diseases, vol. 8, No. 11, Nov. 2002, p. 1187.
Remington: The Science and Practice of Pharmacy, Mack Publishing Company, Easton, Pa, 19th edition, 1995 (book).
Schwab et al., Patterns of Epithelial Cell Invasion by Difference Species of the *Burkholderia cepacia* Complex in Well-Differentiated Human Airway Epithelia, Infect Immun. Aug. 2002;70(8):4547-55.
Singh et al., Quorum-sensing signals indicate that cystic fibrosis lungs are infected with bacterial biofilms, Nature. Oct. 2000 12;407(6805):762-4.
Smith, et al., Pulmonary Deposition and Clearance of Aerosolized Alpha-1-Proteinase Inhibitor Administered to Dogs and to Sheep, J. Clin. Invest. 1989;84:1145-1146.
Stepanovic et al., A modified microtiter-plate test for quantification of *Staphylococcal* biofilm formation, J Microbiol Methods. Apr. 2000;40(2):175-9.
Stewart and Costerton, Antibiotic resistance of bacteria in biofilms, Lancet. Jul. 14, 2001;358(9276):135-8.
Taccetti et al., Multiresistant non-fermentative Gram-negative bacteria in cystic fibrosis patients: the results of an Italian multicenter study, Eur J Epidemiol. 1999 Jan;15(1):85-8.
Tomlin et al., Interspecies biofilms of *Pseudomonas aeruginosa* and *Gburkholderia cepacia*, Can J Microbiol. Oct. 2001;47(10):949-54.
Vaara, Agents That Increase the Permeability of the Outer Membrane, Microbiol Rev. Sep. 1992;56(3):395-411.
van den Hoogen et al., a newly discovered human pneumovirus isolated from young children with respiratory tract disease, 2001, Nature Medicine 7: 719-724.
Pamp et al., The Biofilm Mode of Life: Mechanisms and Adaptations, Horizon Bioscience, 2011, Chapter 4, The Biofilm Matrix: A Sticky Framework by Sünje Johanna Pamp, Morten Gjermansen and Tim Tolker-Nielsen, p. 57. Available Online: http://www.open-access-biology.com/biofilms/biofilmsch4.pdf.

\* cited by examiner

|  | 15 Minutes | | 30 Minutes | |
|---|---|---|---|---|
|  | Colonies/ml | Log Killing | Colonies/ml | Log Killing |
| Start | 3900000 | 0 | | |
| NE | 120000 | 1.51 | 3830 | 3.01 |
| NE + 2.5mM EDTA | 1350 | 3.46 | 0 | 6.59 |
| NE + 5mM EDTA | 630 | 3.79 | 0 | 6.59 |
| NE + 10mM EDTA | 80 | 4.69 | 0 | 6.59 |
| NE + 15mM EDTA | 40 | 4.99 | 0 | 6.59 |
| NE + 20mM EDTA | 0 | 6.59 | 0 | 6.59 |
| 10% Bleach | 0 | 6.59 | | |

| Co-Culture | Start | | NE ALONE | | NE + EDTA | | EDTA | | BLEACH | |
|---|---|---|---|---|---|---|---|---|---|---|
| | Log Killing | Colonies/ml | Log Killing | Colonies/ml | Log Killing | Colonies/ml | Log Killing | Colonies/ml | Log Killing | Colonies/ml |
| B. cepacia (HI 3802) | 0 | 2400000 | 1.38 | 70000 | 6.38 | 0 | 0.66 | 530000 | 6.38 | 0 |
| P. aeruginosa (PA 01) | 0 | 187500 | 1.56 | 0 | 5.27 | 0 | 5.27 | 0 | 5.27 | 0 |

FIGURE 11

| Species (no. tested) | MIC (µg/ml CPC) | | |
|---|---|---|---|
| | 50% | 90% | Range |
| *Burkholderia* species | | | |
| B. cepacia (5) | 62.5 | 125 | 31.2 – 125 |
| B. multivorans (10) | 62.5 | 125 | 31.2 – 125 |
| B. cenocepacia (20) | | | ≤ 15.6 – 500 |
| B. stabilis (5) | | | ≤ 15.6 – 125 |
| B. vietnamiensis (5) | | | ≤ 15.6 – 62.5 |
| B. dolosa (5) | | | 62.5 – 125 |
| B. ambifaria (5) | | | 31.2 – 62.5 |
| B. anthina (5) | | | 31.2 – 62.5 |
| B. pyrrocinia (5) | | | 31.2 – 125 |
| B. gladioli (10) | 31.2 | 125 | ≤ 15.6 – 125 |
| P. aeruginosa (20) | 31.2 | 62.5 | ≤ 15.6 – 62.5 |
| A. xylosoxidans (10) | 31.2 | 62.5 | 31.2 – 62.5 |
| S. maltophilia (15) | ≤ 15.6 | 31.2 | ≤ 15.6 – 62.5 |
| Acinetobacter (10) | ≤ 15.6 | 125 | ≤ 15.6 – 125 |
| *Pandoraea* species | | | |
| P. apista (2) | | | 31.2 |
| P. norimbergensis (2) | | | 31.2 |
| P. pnomenusa (2) | | | 31.2 |
| P. pulmonicola (2) | | | 31.2 – 62.5 |
| P. sputorum (2) | | | 31.2 – 62.5 |
| *Ralstonia* species | | | |
| R. mannitolilytica (5) | | | ≤ 15.6 – 31.2 |
| R. pickettii (5) | | | ≤ 15.6 |
| Total (150) | 31.2 | 125 | ≤ 15.6 – 500 |

FIGURE 12

| Strain | Species | MIC | MBC | MBIC | MBEC | SMBC |
|---|---|---|---|---|---|---|
| AU8042 | B. multivorans | 125 | 125 | 1000 | 1000 | 1000 |
| AU10398b | B. multivorans | 62.5 | 62.5 | 500 | 500 | 250 |
| ATCC 17616 | B. multivorans | 62.5 | 62.5 | 1000 | 1000 | 1000 |
| AU10321 | B. cenocepacia | 31.2 | 31.2 | 1000 | 1000 | 1000 |
| J2315 | B. cenocepacia | 62.5 | 125 | 500 | 1000 | 1000 |
| AU4757 | B. stabilis | 125 | 125 | 500 | 500 | 500 |
| AU10529 | B. gladioli | ≤15.6 | ≤15.6 | 62.5 | 62.5 | 31.2 |
| AU13206 | A. xylosoxidans | 62.5 | 125 | 500 | 2000 | 1000 |
| AU12828 | P. aeruginosa | 31.2 | 31.2 | 1000 | 1000 | 500 |
| AU8215a | P. aeruginosa | 31.2 | 31.2 | 31.2 | 31.2 | 62.5 |
| AU12914 | R. pickettii | ≤15.6 | ≤15.6 | ≤15.6 | ≤15.6 | 31.2 |
| AU4194 | S. maltophilia | ≤15.6 | ≤15.6 | 31.2 | 31.2 | 31.2 |

Values represent μg/ml CPC. SMBC is MBC in the presence of 43% CF sputum.

FIGURE 17

| CPC conc. | (CPC %) | Soybean oil | Poloxomer 407 | Ethanol | CPC% | EDTA | H2O | EDTA mM | CPC mg/ml |
|---|---|---|---|---|---|---|---|---|---|
| 10 mg | 1% | 62.7900 | 5.9200 | 6.7300 | 1.0680 | 0.074500 | 23.4175 | 2.0000 | 10.0000 |
| 5 mg | 0.50% | 31.4000 | 2.9600 | 3.3700 | 0.5300 | 0.037000 | 61.7030 | 1.0000 | 5.0000 |
| 3 mg | 0.3 | 18.8370 | 1.7760 | 2.0190 | 0.3204 | 0.022350 | 77.0253 | 0.6000 | 3.0000 |
| 2.5 mg | 0.25% | 15.7000 | 1.4800 | 1.6600 | 0.2700 | 0.019000 | 80.8510 | 0.5000 | 2.5000 |
| 1000 ug | 0.1 | 6.2780 | 0.5920 | 0.6730 | 0.1068 | 0.007450 | 92.3418 | 0.2000 | 1.0000 |
| 500 ug | 0.05 | 3.1395 | 0.2960 | 0.3365 | 0.0534 | 0.003725 | 96.1709 | 0.1000 | 0.5000 |
| 250 ug | 0.025 | 1.5698 | 0.1480 | 0.1683 | 0.0267 | 0.001853 | 98.0854 | 0.0500 | 0.2500 |
| 10 ug | 0.001 | 0.0628 | 0.0059 | 0.0067 | 0.0011 | 0.000075 | 99.9234 | 0.0020 | 0.0100 |
| 3 ug | 0.003 | 0.1884 | 0.0178 | 0.0202 | 0.0032 | 0.000224 | 99.7703 | 0.0060 | 0.0300 |
| 1 ug | 0.0001 | 0.0063 | 0.0006 | 0.0007 | 0.0001 | 0.000007 | 99.9923 | 0.0002 | 0.0010 |
| 0.1 ug | 0.00001 | 0.0006 | 0.0001 | 0.0001 | 0.0000 | 0.000001 | 99.9992 | 0.0000 | 0.0001 |

NANOEMULSION THERAPEUTIC COMPOSITIONS AND METHODS OF USING THE SAME

This application claims priority to U.S. Provisional Patent Application Ser. No. 60/927,309, filed May 2, 2007, hereby incorporated by reference in its entirety.

FIELD OF THE INVENTION

The present invention relates to methods and compositions useful for treating pulmonary infection. In particular, the present invention provides nanoemulsion compositions and methods of using the same to treat bacteria associated with biofilms (e.g., found in pulmonary infections). Compositions and methods of the present invention find use in, among other things, clinical (e.g. therapeutic and preventative medicine), industrial, and research applications.

BACKGROUND OF THE INVENTION

Invasion of the respiratory tract is a common route for microbes to establish infection.

Certain types of individuals are prone to respiratory infection (e.g., by bacteria (e.g., opportunistic bacteria), viruses, fungi and/or parasites) including the immunocompromised, elderly, cancer chemotherapy patients, individuals suffering from asthma, individual suffering from genetically inherited disease (e.g., cystic fibrosis) and virally infected individuals (e.g., infected with influenza virus, respiratory syncytial virus (RSV), adenovirus and/or human immunodeficiency virus).

A serious consequence of cystic fibrosis (CF) is *Pseudomonas aeruginosa* lung infection, which by itself accounts for almost 90% of the morbidity and mortality in CF (See e.g., Cystic Fibrosis Foundation. Patient Registry 1994 annual data report, Bethesda, Md. 1995). By age 12, 60-90% of CF patients are infected with *P. aeruginosa*, and most die before age 30. Pathogens such as *Staphylococcus aureus* and nontypable *H. influenza* are also commonly isolated from the respiratory tract of CF patients. Progressive loss of pulmonary function over many years due to chronic infection with mucoid *P. aeruginosa* is the hallmark of CF.

Asthma is a disorder of the respiratory system characterized by airway hyperresponsiveness leading to acute and/or chronic airway inflammation. The severity of hyperreactivity typically correlates with the degree of inflammation. Mucus hyper-secretion and mucus cell hyperplasia are seen in the lungs of patients with asthma. In chronic asthmatic individuals, mucus forms a viscoelastic gel, which is very sticky. When it stagnates, mucus can occlude the airway and become a favorable locus for bacteria or disease pathogenesis.

SUMMARY OF THE INVENTION

The present invention relates to methods and compositions useful for treating pulmonary infection. In particular, the present invention provides nanoemulsion compositions and methods of using the same to treat bacteria associated with biofilms (e.g., found in pulmonary infections). Compositions and methods of the present invention find use in, among other things, clinical (e.g. therapeutic and preventative medicine), industrial, and research applications.

Accordingly, in some embodiments, the present invention provides a method of treating a subject comprising: providing a subject, wherein the subject exhibits signs and/or symptoms of a respiratory infection or has a respiratory infection: a composition comprising a nanoemulsion; and administering the composition to the subject under conditions such that the signs and/or symptoms of respiratory infection are ameliorated in the subject. In some embodiments, the respiratory infection is a microbial infection. In some embodiments, the subject is a subject with bronchitis, a subject with bronchiectasis, a subject with pneumonia, a subject with tuberculosis, a subject with cystic fibrosis, a subject with emphysema radiation pneumonitis, or any other type of subject at risk for respiratory infection as described herein. In some embodiments, the microbial infection comprises bacterial infection, fungal infection, viral infection, or combination of two or more of the same. In some embodiments, the bacterial infection is caused by an opportunistic and/or pathogenic bacteria (e.g., *Burkholderia cepacia* and *Pseudomonas aeruginosa*).

In some embodiments, the present invention provides a composition comprising a nanoemulsion and a chelating agent (e.g., ethylenediaminetetraacetic acid (EDTA)), and methods of pulmonary administrating the same to prevent and/or treat respiratory infection. In some embodiments, the composition is co-administered with a hypertonic salt (e.g., sodium chloride) solution (e.g., a 6-7% NaCl solution). In some embodiments, the composition comprises a 20% nanoemulsion solution. In some embodiments, the composition comprises greater than 20% (e.g., 25%, 30%, or more) nanoemulsion solution. In some embodiments, the composition comprises less than 20% (e.g., 15%, 10% or less) nanoemulsion solution. However, the present invention is not limited to this amount (e.g., percentage) of nanoemulsion. For example, in some embodiments, a composition comprises less than 10% nanoemulsion. In some embodiments, a composition comprises more than 20% nanoemulsion. In some embodiments, the composition comprises 10 mM EDTA. In some embodiments, the composition comprises 20 mM EDTA. In some embodiments, the composition comprises less than 10 mM or more than 20 mM EDTA. In some embodiments, a composition of the present invention comprises any of the nanoemulsions described herein. In some embodiments, the nanoemulsion comprises $P_{407}5EC$. In some embodiments, the nanoemulsion comprises $W_{80}5EC$. In some embodiments, the nanoemulsion comprises $W_{20}5EC$. In some embodiments, the nanoemulsion comprises $W_{80}8P$. The present invention is not limited by the type of nanoemulsion utilized. Indeed, a variety of nanoemulsions are contemplated to be useful in the present invention. For example, in some preferred embodiments, the nanoemulsion (e.g., for pulmonary administration (e.g., to treat or prevent respiratory infection)) comprises an oil-in-water emulsion, the oil-in-water emulsion comprising a discontinuous oil phase distributed in an aqueous phase, a first component comprising a solvent (e.g., an alcohol or glycerol), and a second component comprising a surfactant or a halogen-containing compound. The aqueous phase can comprise any type of aqueous phase including, but not limited to, water (e.g., $diH_2O$, distilled water, tap water) and solutions (e.g., phosphate buffered saline solution). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In some preferred embodiments, the oil phase comprises 30-90 vol % of the oil-in-water emulsion (i.e., constitutes 30-90% of the total volume of the final emulsion), more preferably 50-80%. While the present invention in not limited by the nature of the alcohol component, in some preferred embodiments, the alcohol is ethanol or methanol. Furthermore, while the present invention is not limited by the nature of the surfactant, in some preferred embodiments, the surfactant is a polysorbate surfactant (e.g., TWEEN 20, TWEEN 40, TWEEN 60, and TWEEN 80), a pheoxypolyethoxyethanol (e.g., TRITON X-100, X-301, X-165, X-102, and X-200, and TYLOXAPOL) or sodium dodecyl sulfate. Likewise, while the present invention is not limited by the nature of the halogen-containing compound, in some preferred embodiments, the halogen-containing compound comprises a cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyidimethylethylammonium bromide, cetyltributylphosphonium bromide, dodecyltrimethylammonium bromide, or tetrad ecyltrimethylammonium bromide. Nanoemulsions of the present invention may further comprise third, fourth, fifth, etc. components. In some preferred embodiments, an additional component is a surfactant (e.g., a second surfactant), a germination enhancer, a phosphate based solvent (e.g., tributyl phosphate), a neutramingen, L-alanine, ammonium chloride, trypticase soy broth, yeast extract, L-ascorbic acid, lecithin, p-hyroxybenzoic acid methyl ester, sodium thiosulate, sodium citrate, inosine, sodium hydroxide, dextrose, and polyethylene glycol (e.g., PEG 200, PEG 2000, etc.). In some embodiments, the oil-in-water emulsion comprises a quaternary ammonium compound. In some preferred embodiments, the oil-in-water emulsion has no detectable toxicity to plants or animals (e.g., to humans). In other preferred embodiments, the oil-in-water emulsion causes no detectable irritation to plants or animals (e.g., to humans). In some embodiments, the oil-in-water emulsion further comprises any of the components described above. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy) ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl)ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride. In some embodiments, the emulsion lacks any antimicrobial substances (i.e., the only antimicrobial composition is the emulsion itself). In some embodiments, the nanoemulsion is X8P. In some embodiments, the nanoemulsion is $P_{407}5EC$. In some embodiments, administration of a nanoemulsion of the present invention protects the subject from displaying signs or symptoms of disease (e.g., caused by one or microbes and/or pathogens (e.g., pathogenic bacteria)) residing in the pulmonary system (e.g., *Burkhoderia cepacia* and *Pseudomonas aeruginosa*). In some embodiments, administration of a nanoemulsion (e.g., pulmonary administration (e.g., to treat or prevent pulmonary infection)) protects a subject from morbidity and/or mortality associated with respiratory infection. In some embodiments, the subject is a human.

In some embodiments, the present invention provides a method for killing and/or inhibiting growth of bacteria associated with a biofilm comprising: providing: bacteria associated with a biofilm; and a composition comprising: a nanoemulsion and ethylenediaminetetraacetic acid (EDTA), wherein the nanoemulsion comprises: a) about 5 vol. % of Poloxamer-407; b) about 8 vol. % of ethanol; c) about 1 vol. % of cetylpyridinium chloride (CPC); d) about 64 vol. % of oil (e.g., soybean oil), and e) about 22 vol. % of water; and exposing the bacteria associated with a biofilm to the composition under conditions such that the composition kills and/or inhibits growth of the bacteria. In some embodiments, the composition further comprises a hypertonic salt solution. In some embodiments, the hypertonic salt solution is a 7% sodium chloride solution. In some embodiments, the nanoemulsion further comprises 10 mM-20 mM EDTA, although the nanoemulsion may comprise less than 10 mM or greater than 20 mM EDTA. In some embodiments, the nanoemulsion comprises 20 mM EDTA. In some embodiments, the nanoemulsion comprises droplets having an average diameter of about 400 nM. In some embodiments, the nanoemulsion is administered via pulmonary administration. In some embodiments, a nebulizer is utilized for the pulmonary administration. In some embodiments, the nanoemulsion is co-administered with an antimicrobial agent. In some embodiments, the composition comprises 20% nanoemulsion. In some embodiments, bacteria associated with a biofilm reside within the pulmonary system of a subject. In some embodiments, the subject displays signs and/or symptoms of a respiratory infection. In some embodiments, bacteria associated with a biofilm reside on and/or within a subject with cystic fibrosis. In some embodiments, the bacteria associated with a biofilm are *Burkholderia cepacia* and *Pseudomonas aeruginosa*. The present invention is not limited by the type of bacteria treated (e.g., killed and/or growth inhibited) with a composition described herein. Indeed, a variety of bacteria (e.g., associated with a biofilm) can be treated including, but not limited to, *Acinetobacter* species, *Burkholderia multivorans, B. cenocepacia, B. stabilis, B. vietnamiensis, B. dolosa, B. ambifaria, B. anthina, B. pyrrocinia, B. gladioli, Achromobacter xylosoxidans, Stenotrophomonas maltophilia, Pandoraea apista, Pandoraea pnomenusa, Pandoraea pulmonicola, Pandoraea norimburgensis, Pandoraea sputorum, Ralstonia mannitolilytica, Ralstonia pickettii, Haemophilus influenza, Staphylococcus aureus*, and *Staphylococcus epidermidis.*

The present invention also provides a composition comprising: a nanoemulsion; ethylenediaminetetraacetic acid (EDTA); and a hypertonic salt solution. In some embodiments, the composition comprises 20 mM EDTA. In some embodiments, the nanoemulsion comprises: a) about 5 vol. % of Poloxamer-407; b) about 8 vol. % of ethanol; c) about 1 vol. % of cetylpyridinium chloride (CPC); d) about 64 vol. % of oil (e.g., soybean oil), and e) about 22 vol. % of water. In some embodiments, the hypertonic salt solution is a 7% sodium chloride solution. In some embodiments, the composition is an aerosolized solution. In some embodiments, the nanoemulsion comprises droplets having an average diameter of about 400 nM. In some embodiments, the nanoemulsion droplets have an average diameter selected from the group comprising less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof.

The present invention also provides a kit comprising a nanoemulsion configured to treat and/or prevent respiratory infection (e.g., caused by *B. cepacia* and/or *P. aeruginosa*) in a subject. In some embodiments, the kit further comprises instructions for administering the composition. In some embodiments, the kit further comprises a device for administering the composition. The present invention is not limited by the type of device utilized for administering the composition. Indeed, a variety of devices are contemplated to be useful in a kit including, but not limited to, a nasal applicator, a syringe, a nasal inhaler and a nasal mister and/or nebulizer. In some embodiments, the kit comprises a composition comprising a nanoemulsion in contact with a device (e.g., an applicator). In some embodiments, the present invention provides systems and methods for sterile administration of a composition of the present invention.

DESCRIPTION OF THE DRAWINGS

FIG. 1 shows killing of *Burkholderia cepacia* in PBS by 20% Nanemulsion (NE) alone or with 20 mM EDTA in 10 minutes.

FIG. 2 shows killing of *B. cepacia* in PBS by 20% NE alone or with 20 mM EDTA in 20 minutes.

FIG. 3 shows killing of *B. cepacia* in PBS by 20% NE alone or with 20 mM EDTA in 40 minutes.

FIG. 4 shows (A) killing of *B. cepacia* in PBS by 20% NE alone or with 20 mM EDTA in 40 minutes; (B) killing of *B. cepacia* in PBS by 20% NE alone or with 20 mM EDTA in 60 minutes; and (C) killing of *B. cepacia* in PBS by 20% NE alone or with 20 mM EDTA in 60 minutes.

FIG. 5 shows killing of *B. cepacia* in hypertonic saline (6% NaCl) at 15 and 30 Minutes by NE alone and NE with EDTA.

FIG. 6 shows killing of *B. cepacia* and *P. aeruginosa* in 7% NaCl within 15 min.

FIG. 7 shows killing of *B. cepacia* and *P. aeruginosa* (Mixed-culture) in 7% NaCl within 15 minutes.

FIG. 8 shows a microtiter serial dilution MIC assay. Numbers above the plate indicate the concentration (μg/ml CPC) of $P_{407}$5EC added to each column of wells. The bacterial species added to wells in each row is indicated on the left. The MICs for these strains (top to bottom) are ≤15.6 μg/ml, 125 μg/ml, and 31.2 μg/ml.

FIG. 9 shows distribution of $P_{407}$5EC MICs for 150 *Burkholderia* and non-*Burkholderia* strains FIG. 10 shows a time-kill study of $P_{407}$5EC activity and concentration-dependent inhibition of $P_{407}$5EC activity by CF sputum. (A) $10^5$ CFU/ml of *B. multivorans* ATCC 17616 were exposed to various concentrations of $P_{407}$5EC around the MIC (62.5 μg/ml) and viable bacterial counts were determined at the times indicated. (B) $10^5$ CFU/ml of *B. multivorans* ATCC 17616 were exposed to various concentrations of $P_{407}$5EC in the presence of three concentrations of CF sputum for 24 hr before viable bacterial counts were determined. Numbers and symbols in inset boxes indicate concentrations of $P_{407}$5EC (μg/ml CPC) used.

FIG. 11 shows in vitro activity of $P_{407}$5EC.

FIG. 12 shows in vitro activity of $P_{407}$5EC against biofilm bacteria and in the presence of CF sputum.

FIG. 13 shows influence of $P_{407}$5EC on *B. cepacia, P. aeruginosa* and *E. coli* individual biofilms.

FIG. 14 shows influence of $P_{407}$5EC on mixed biofilms.

FIG. 15 shows influence of $P_{407}$5EC on mixed biofilms.

FIG. 16 shows influence of $P_{407}$5EC on escape colonies of *B. cepacia* biofilms.

FIG. 17 shows serial, two-fold dilutions of $P_{407}$5EC in one embodiment of the invention.

DEFINITIONS

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein, the term "pathogen" refers a biological agent that causes a disease state (e.g., infection, sepsis, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red. In some embodiments, bacteria are continuously cultured. In some embodiments, bacteria are uncultured and existing in their natural environment (e.g., at the site of a wound or infection) or obtained from patient tissues (e.g., via a biopsy). Bacteria may exhibit pathological growth or proliferation. Examples of bacteria include, but are not limited to, bacterial cells of a genus of bacteria selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira*, and *Chlamydiae*.

As used herein, the terms "microorganism" and "microbe" refer to any species or type of microorganism, including but not limited to, bacteria, archaea, fungi, protozoans, mycoplasma, and parasitic organisms.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

"Respiratory" and "respiration" refer to the process by which oxygen is taken into the body and carbon dioxide is discharged, through the bodily system including the nose, throat, larynx, trachea, bronchi and lungs.

"Respiratory infection" and "pulmonary infection" refer to an infection (e.g., bacterial, viral, fungal, etc.) of the respiratory tract. In humans, the respiratory tract comprises the upper respiratory tract (e.g., nose, throat or pharynx, and larynx); the airways (e.g.: voice box or larynx, windpipe or trachea, and bronchi); and the lungs (e.g., bronchi, bronchioles, alveolar ducts, alveolar sacs, and alveoli).

"Respiratory disease", "pulmonary disease," "respiratory disorder", "pulmonary disorder," "respiratory condition", "pulmonary condition," "pulmonary syndrome," and "respiratory syndrome" refer to any one of several ailments that involve inflammation and affect a component of the respiratory system including especially the trachea, bronchi and lungs. Examples of such ailments include acute alveolar disease, obstructive respiratory disease (e.g., asthma; bronchitis; and chronic obstructive pulmonary disease, referred to as COPD), upper airway disease (e.g., such as otitis media, and rhinitis/sinusitis), interstitial lung disease, allergy, and respiratory infection (e.g., pneumonia, pneyumocystis carinii, and respiratory syncitial virus (RSV)).

Specific examples of acute alveolar disease include acute lung injury (ALI), acute respiratory distress syndrome (ARDS), meconium aspiration syndrome (MAS) and respiratory distress syndrome (RDS). ALI is associated with conditions that either directly or indirectly injure the air sacs of the lung, the alveoli. ALI is a syndrome of inflammation and increased permeability of the lungs with an associated breakdown of the lungs' surfactant layer. The most serious manifestation of ALI is ARDS. Among the causes of ALI are complications typically associated with certain major surgeries, mechanical ventilator induced lung injury (often referred to as VILI), smoke inhalation, pneumonia, and sepsis.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention.

As used herein, the terms "inactivating," "inactivation" and grammatical equivalents, when used in reference to a microorganism refer to the killing, elimination, neutralization and/or reducing the capacity of the mircroorganism to infect and/or cause a pathological response and/or disease in a host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium, bacterial spore, or bacterial biofilm). In preferred embodiments of the present invention, the presence of a lysogenic and a fusigenic agent in the same composition produces an enhanced inactivating effect compared to either agent alone. Methods and compositions using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsions comprise an oil phase having droplets with a mean particle size of approximately 0.1 to 5 microns (e.g., in some embodiments, the particle size is 0.1-0.8 microns in diameter, in other embodiments, the particle size is 0.1-0.5 microns in diameter), although smaller and larger particle sizes are contemplated (e.g., 0.01-0.1 microns in diameter, 0.1-0.3 microns in diameter, 0.15-0.40 microns in diameter, 0.3-0.6 microns in diameter, and 0.5-0.8 microns in diameter). The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion kill and/or attenuate growth of the microorganism or pathogenic agent, if present. The present invention is not limited by the amount or type of nanoemulsion used for microorganism killing and/or growth attenuation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion are contemplated in the present invention including, but not limited to, those described herein (e.g., in Examples 1-4, the Figures associated therewith and FIG. 17).

The term "surfactant" refers to any molecule having both a polar head group, which energetically prefers salvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope. Contemplated interaction enhancers include, but are not limited to, chelating agents (e.g., ethylenediaminetetraacetic acid (EDTA), ethylenebis(oxyethylenenitrilo)tetraacetic acid (EGTA), and the like) and certain biological agents (e.g., bovine serum abulmin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

In some embodiments of the invention, a nanoemulsion composition comprises a nanoemulsion and one or more interaction enhancers. In further preferred embodiments, the composition comprising a nanoemulsion and one or more interaction enhancers comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. Thus, in some preferred embodiments, a composition comprising a nanoemulsion and one or more interaction enhancers is administered to a subject to prevent or attenuate a respiratory infection (e.g., thereby providing the total or partial attenuation (e.g., suppression) of a sign, symptom or condition of the infection or disease associated therewith)).

As used herein, the term "effective amount" refers to the amount of a composition (e.g., a composition comprising a nanoemulsion) sufficient to effect a beneficial or desired result (e.g., to treat and/or prevent infection (e.g., through bacterial cell killing and/or prevention of bacterial cell growth). An effective amount can be administered in one or more administrations, applications or dosages and is not intended to be limited to a particular formulation or administration route.

As used herein, the term "immune response" refers to any detectable response by the immune system of a subject. For example, immune responses include, but are not limited to, an alteration (e.g., increase) in Toll receptor activation, lymphokine (e.g., cytokine (e.g., Th1 or Th2 type cytokines) or chemokine) expression and/or secretion, macrophage activation, dendritic cell activation, T cell (e.g., CD4+ or CD8+ T cell) activation, NK cell activation, and/or B cell activation (e.g., antibody generation and/or secretion). Additional examples of immune responses include binding of an immunogen (e.g., antigen (e.g., immunogenic polypeptide)) to an MHC molecule and induction of a cytotoxic T lymphocyte ("CTL") response, induction of a B cell response (e.g., antibody production), and/or T-helper lymphocyte response, and/or a delayed type hypersensitivity (DTH) response (e.g., against the antigen from which an immunogenic polypeptide is derived), expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to an antigen and/or immunogen (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression of) a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "enhanced immunity" refers to an increase in the level of adaptive and/or acquired immunity in a subject to a given immunogen (e.g., microorganism (e.g., pathogen)) following administration of a composition relative to the level of adaptive and/or acquired immunity in a subject that has not been administered the composition.

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a drug, prodrug, or other agent, or therapeutic treatment (e.g., a composition of the present invention) to a physiological system (e.g., a subject or in vivo, in vitro, or ex vivo cells, tissues, and organs).

As used herein, the terms "co-administration" and "co-administering" refer to the administration of at least two agent(s) (e.g., a nanoemulsion and one or more other pharmaceutically acceptable substances (e.g., a second nanoemulsion)) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to treat and/or prevent infection by more than one type of infectious agent (e.g., bacteria and/or viruses).

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

Compositions of the present invention can be applied using any pharmaceutically acceptable method, such as for example, intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, mucosally administered, via an aerosol, or via a buccal or nasal spray formulation. Further, the nanoemulsion vaccine can be formulated into any pharmaceutically acceptable dosage form, such as a liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof.

The terms "pharmaceutically acceptable" or "pharmacologically acceptable," as used herein, refer to compositions that do not substantially produce adverse reactions (e.g., toxic, allergic or pathological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the terms "at risk for disease" and "at risk for infection" refer to a subject that is predisposed to experiencing a particular disease and/or infection. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people that carry a risk of transmitting a pathogen), nor is it intended that the present invention be limited to any particular disease and/or infection.

"Nasal application", as used herein, means applied through the nose into the nasal or sinus passages or both. The application may, for example, be done by drops, sprays, mists, coatings or mixtures thereof applied to the nasal and sinus passages.

"Pulmonary application" and "pulmonary administration" refers to any means of applying a composition of the present invention to the pulmonary system of a subject. The present invention is not limited to any particular means of administration. Indeed, a variety of means are contemplated to be useful for pulmonary administration including those described herein.

As used herein, the term "kit" refers to any delivery system for delivering materials. In the context of the nanoemulsion compositions of the present invention, such delivery systems include systems that allow for the storage, transport, or delivery of the compositions and/or supporting materials (e.g., written instructions for using the materials, etc.) from one location to another. For example, kits include one or more enclosures (e.g., boxes) containing the relevant nanoemulsions and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of a composition needed for a particular use in a single container (e.g., in a single box housing each of the desired components). The term "kit" includes both fragmented and combined kits.

DETAILED DESCRIPTION OF THE INVENTION

The present invention relates to methods and compositions useful for treating pulmonary infection. In particular, the present invention provides nanoemulsion compositions and methods of using the same to treat bacteria associated with biofilms (e.g., found in pulmonary infections). Compositions and methods of the present invention find use in, among other things, clinical (e.g. therapeutic and preventative medicine), industrial, and research applications.

Several pathogenic microorganisms initiate infection by attaching to mucosal epithelial cells lining the gastro-intestinal, oropharyngeal, respiratory or genito-urinacy tracts. Some pathogens, such as influenza virus, *Bordetella pertussis*, or *Vibrio cholerae*, remain at or within the mucosal tissue, while others, such as *Salmonella typhi* or hepatitis A virus, possess mechanisms permitting penetration into deeper tissues and spread systemically. Specific and non-specific defense mechanisms of the mucous membranes provide first line protection against both types of pathogen. Non-specific effectors include resident macrophages, antimicrobial peptides, lactoferrin and lysozyme, extremes of pH, bile acids, digestive enzymes, mucus, shedding of epithelial cells, flushing mechanisms (peristalsis, ciliary beating, micturation, etc.) and competition from local flora. However, successful pathogens have generally evolved means to survive the non-specific defenses present at the site they infect and it is the secretory immune system which plays a major role in protecting against diseases caused by a number of bacterial and viral pathogens, and is probably a major effector against pathogens that are restricted to mucosal surfaces. For organisms that spread systemically, both local and systemic immune responses are desirable for optimum immunity.

As described herein, certain microbes (e.g., bacteria) are able to thrive when a normal and/or healthy immune system does not function properly for one reason or another. Cystic fibrosis (CF), asthma, HIV infection, chemotherapeutic therapy and a host of other conditions lead to malfunctioning and/or attenuation of immune responses that would normally function to protect against and clear microbes capable of causing pathology in a healthy subject.

Cystic Fibrosis (CF) is one of the most common fatal genetic disorders in the United States. CF is most prevalent in the Caucasian population and occurs on an average of one in every 3,300 live births. A mutation in a gene that encodes a chloride channel—the cystic fibrosis transmembrane conductance regulator—produces partially functional or completely dysfunctional channels. Depending on where the gene is mutated and/or whether the person carries one or two copies of the mutated allele, the prognosis varies widely: heterozygous individuals are fine for life; those who are homozygous for the mutation get CF; and if patients have the most common CF allele—DF508—they typically die at the age of 31. CF is characterized by chronic respiratory infection that begins early in life with *Staphylococcus aureus* and *Haemophilus influenzae* infections and later colonization with mucoid strains of *Pseudomonas aeruginosa*.

*Pseudomonas aeruginosa* is an opportunistic pathogen that infects the immunocompromised, elderly, cancer chemotherapy patients, and individual suffering from CF. In CF lung disease, *P. aeruginosa* is trapped in thickened, dehydrated, hypoxic mucus lining in airway epithelia. Morphologic data suggests that the airway lumen of CF patients harbor *P. aeruginosa* biofilms that are characterized as spherical microcolonies.

Other types of microbes can cause pathology in an otherwise healthy host subject. For example, colonization of the respiratory tract by the Gram-negative coccobacillus *Bordetella pertussis* results in whooping cough, also called pertussis, a significant cause of morbidity and mortality of human infants. Two other closely-related isolates of *Bordetella* have also been found in humans: *B. parapertussis* and *B. bronchiseptica*. Molecular genetic analyses suggest that these three isolates are too closely related to be classified as separate species. (See Gilchrist. M. J. R., 1991, "Bordetella", in Manual of Clinical Microbiology, 5th ed., Balows, A. et al., eds., American Society for Microbiology, Washington, D.C.). While *B. pertussis* differs from *B. bronchiseptica* and B. parapertussis in the nature of the toxins it produces, *B. bronchiseptica* and *B. parapertussis* do produce active toxins (See Hausman, S. Z. et al., 1996, Infect. Immun. 64: 4020-4026), and there is some evidence to indicate that *B. pertussis* organisms can covert to the *B. parapertussis* phenotype (Gilchrist, M. J. R., 1991, "Bordetella", in Manual of Clinical Microbiology, 5th ed., Balows, A. et al., eds., American Society for Microbiology, Washington, D.C.).

Symptoms of upper respiratory infection include runny or stuffy nose, irritability, restlessness, poor appetite, decreased activity level, coughing, and fever. Viral upper respiratory infections cause and/or are associated with sore throats, colds, croup, and the flu. Examples of viruses that cause upper respiratory tract infections include rhinoviruses and influenza viruses A and B. Common upper respiratory bacterial infections cause and/or associated with, for example, whooping cough and strep throat. An example of a bacterium that causes an upper respiratory tract infection is *Streptococcus*.

Clinical manifestations of a lower respiratory infection include shallow coughing that produces sputum in the lungs, fever, and difficulty breathing. Examples of lower respiratory viral infections are parainfluenza virus infections ("PIV"), respiratory syncytial virus ("RSV"), and bronchiolitis. Examples of bacteria that cause lower respiratory tract infections include *Streptococcus pneumoniae* that causes pneumonococcal pneumonia and *Mycobacterium tuberculosis* that causes tuberculosis. Respiratory infections caused by fungi include systemic candidiasis, blastomycosis crytococcosis, coccidioidomycosis, and aspergillosis. Respiratory infections may be primary infections, or may be secondary infections (e.g., secondary to infection by another microbe (e.g., a viral infection)).

Current therapies for respiratory infections involve the administration of anti-viral agents, anti-bacterial, and anti-fungal agents for the treatment, prevention, or amelioration of viral, bacterial, and fungal respiratory infections, respectively. Unfortunately, in regard to certain infections, there are no therapies available, infections have been proven to be refractory to therapies, or the occurrence of side effects outweighs the benefits of the administration of a therapy to a subject. The use of anti-bacterial agents for treatment of bacterial respiratory infections may also produce side effects or result in resistant bacterial strains. The administration of anti-fungal agents may cause renal failure or bone marrow dysfunction and may not be effective against fungal infection in patients with suppressed immune systems. Additionally, the infection causing microorganism (e.g., virus, bacterium, or fungus) may be resistant or develop resistance to the administered therapeutic agent or combination of therapeutic agents. In fact, microorganisms that develop resistance to administered therapeutic agents often develop pleiotropic drug or multidrug resistance, that is, resistance to therapeutic agents that act by mechanisms different from the mechanisms of the administered agents. Thus, as a result of drug resistance, many infections prove refractory to a wide array of standard treatment protocols. Therefore, new therapies for the treatment, prevention, management, and/or amelioration of respiratory infections and symptoms thereof are needed.

Thus, the present invention provides compositions and methods for the treatment of respiratory infections. Compositions and methods of the present invention may be used to treat and/or prevent respiratory infection (e.g., in cystic fibrosis patients) caused by one or more of pseudomonas (e.g., *P. aeruginosa, P. paucimobilis, P. putida, P. fluorescens* and *P. acidovorans*), staphylococci, Methicillin-resistant *Staphylococcus aureus* (MRSA), streptococci (including *Streptococcus pneumoniae*), *Escherichia coli, Klebsiella, Enterobacter, Serratia, Haemophilus, Yersinia pestis, Burkholderia pseudomallei, B. cepacia, B. gladioli, B. multivorans, B. vietnamiensis, Mycobacterium tuberculosis, M. avium* complex (MAC) (*M. avium* and *M. intracellulare*), *M. kansasii, M. xenopi, M. marinum*, M. ulcerans, or *M. fortuitum* complex (*M. fortuitum* and *M. chelonei*), *Bordetella pertussis, B. parapertussis* and *B. bronchiseptica*. Furthermore, compositions and methods of the present invention find use in the treatment and/or prevention of a host of respiratory infections (e.g., respiratory infections of the upper respiratory tract (e.g., nose, ears, sinuses, and throat) and the lower respiratory tract (e.g., trachea, bronchial tubes, and lungs)). Several examples of microbes that may be treated (e.g., killed and/or attenuated in growth (e.g., within the respiratory tract of a subject)) are provided below.

Viral Respiratory Infections

Parainfluenza Virus Infections. Parainfluenza viral ("PIV") infection results in serious respiratory tract disease in infants and children. (See Tao et al., 1999, Vaccine 17: 1100-08). Infectious parainfluenza viral infections account for approximately 20% of all hospitalizations of pediatric patients suffering from respiratory tract infections worldwide.

PIV is a member of the paramyxovirus genus of the paramyxoviridae family. PIV is made up of two structural modules: (1) an internal ribonucleoprotein core or nucleocapsid, containing the viral genome, and (2) an outer, roughly spherical lipoprotein envelope. Its genome is a single strand of negative sense RNA, approximately 15,456 nucleotides in length, encoding at least eight polypeptides. These proteins include, but are not limited to, the nucleocapsid structural protein (NP, NC, or N depending on the genera), the phosphoprotein (P), the matrix protein (M), the fusion glycoprotein (F), the hemagglutinin-neuraminidase glycoprotein (HN), the large polymerase protein (L), and the C and D proteins of unknown function.

The parainfluenza nucleocapsid protein (NP, NC, or N) consists of two domains within each protein unit including an amino-terminal domain, comprising about two-thirds of the molecule, which interacts directly with the RNA, and a carboxyl-terminal domain, which lies on the surface of the assembled nucleocapsid. A hinge is thought to exist at the junction of these two domains thereby imparting some flexibility to this protein (See Fields et al. (ed.), 1991, Fundamental Virology, 2nd ed., Raven Press, New York, incorporated by reference herein in its entirety). The matrix protein (M), is apparently involved with viral assembly and interacts with both the viral membrane as well as the nucleocapsid proteins. The phosphoprotein (P), which is subject to phosphorylation, is thought to play a regulatory role in transcription and may also be involved in methylation, phosphorylation and polyadenylation. The fusion glycoprotein (F) interacts with the viral membrane and is first produced as an inactive precursor then cleaved post-translationally to produce two disulfide linked polypeptides. The active F protein is also involved in penetration of the parainfluenza virion into host cells by facilitating fusion of the viral envelope with the host cell plasma membrane. The glycoprotein, hemagglutinin-neuraminidase (HN), protrudes from the envelope allowing the virus to contain both hemagglutinin and neuraminidase activities. HN is strongly hydrophobic at its amino terminal which functions to anchor the HN protein into the lipid bilayer. The large polymerase protein (L) plays an important role in both transcription and replication.

Treatment for PIV comprises treatment of specific symptoms. In most cases, rest, fluids, and a comfortable environment are sufficient therapy for PIV infection. For croup associated with PIV infection, therapies such as humidified air, oxygen, aerosolized racemic epinephrine, and oral steroids (e.g., dexamethasone) are recommended to decrease upper airway swelling and intravenous fluids are administered for dehydration. Therapy for bronchiolitis associated with PIV infection include supportive therapy (e.g., oxygen, humidified air, chest clapping, and postural drainage to remove secretions, rest, and clear fluids) and administration of albuterol or steroids. Antibiotic, anti-viral, and/or antifungal agents may be administered to prevent secondary respiratory infections (See Merck Manual of Diagnosis and Therapy (17th ed., 1999)).

Respiratory Syncytial Virus Infections

Respiratory syncytial virus ("RSV") is the leading cause of serious lower respiratory tract disease in infants and children (See Feigen et al., eds., 1987, Textbook of Pediatric Infectious Diseases, W B Saunders, Philadelphia at pages 1653-1675; New Vaccine Development, Establishing Priorities, Vol. 1, 1985, National Academy Press, Washington D.C. at pages 397-409; and Ruuskanen et al., 1993, Curr. Probl. Pediatr. 23: 50-79). The yearly epidemic nature of RSV infection is evident worldwide, but the incidence and severity of RSV disease in a given season vary by region (See Hall, C. B., 1993, Contemp. Pediatr. 10: 92-110). In temperate regions of the northern hemisphere, it usually begins in late fall and ends in late spring. Primary RSV infection occurs most often in children from 6 weeks to 2 years of age and uncommonly in the first 4 weeks of life during nosocomial epidemics (See Hall et al., 1979, New Engl. J. Med. 300: 393-396). Children at increased risk from RSV infection include, but are not limited to, preterm infants (See Hall et al., 1979, New Engl. J. Med. 300: 393-396) and children with bronchopulmonary dysplasia (See Groothuis et al., 1988, Pediatrics 82: 199-203), congenital heart disease (See MacDonald et al., New Engl. J. Med. 307: 397-400), congenital or acquired immunodeficiency (See Ogra et al., 1988, Pediatr. Infect. Dis. J. 7: 246-249; and Pohl et al., 1992, J. Infect. Dis. 165: 166-169), and cystic fibrosis (See Abman et al., 1988, J. Pediatr. 113: 826-830). The fatality rate in infants with heart or lung disease who are hospitalized with RSV infection is 3%-4% (See Navas et al., 1992, J. Pediatr. 121: 348-354).

RSV infects adults as well as infants and children. In healthy adults, RSV causes predominantly upper respiratory tract disease. It has recently become evident that some adults, especially the elderly, have symptomatic RSV infections more frequently than had been previously reported (See Evans, A. S., eds., 1989, Viral Infections of Humans Epidemiology and Control, 3Rd ed., Plenum Medical Book, New York at pages 525-544). Several epidemics also have been reported among nursing home patients and institutionalized young adults (See Falsey, A. R., 1991, Infect. Control Hosp. Epidemiol. 12: 602-608; and Garvie et al., 1980, Br. Med. J. 281: 1253-1254). RSV may cause serious disease in immunosuppressed persons (e.g., bone marrow transplant patients and subjects with HIV (See, e.g. Hertz et al., 1989, Medicine 68: 269-281).

Therapies available for the treatment of established RSV disease are limited. Severe RSV disease of the lower respiratory tract often requires considerable supportive care, including administration of humidified oxygen and respiratory assistance (See, e.g., Fields et al., eds, 1990, Fields Virology, 2nd ed., Vol. 1, Raven Press, New York at pages 1045-1072).

While a vaccine might prevent RSV infection, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (See, e.g., Kim et al., 1969, Am. J. Epidemiol. 89: 422-434; and Kapikian et al., 1969, Am. J. Epidemiol. 89: 405-421). Several candidate RSV vaccines have been abandoned and others are under development (See, e.g., Murphy et al., 1994, Virus Res. 32: 13-36).

Currently, the only approved approach to prophylaxis of RSV disease is passive immunization. Initial evidence suggesting a protective role for IgG was obtained from observations involving maternal antibody in ferrets (See, e.g., Prince, G. A., Ph.D. diss., University of California, Los Angeles, 1975) and humans (Sees e.g., Lambrecht et al., 1976, J. Infect. Dis. 134: 211-217; and Glezen et al., 1981, J. Pediatr. 98: 708-715). Hemming et al. (See, e.g., Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis. They noted that one infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (See, e.g., Prince et al., 1985, Virus Res. 3: 193-206; Prince et al., 1990, J. Virol. 64: 3091-3092; Hemming et al., 1985, J. Infect. Dis. 152: 1083-1087; Prince et al., 1983, Infect. Immun. 42: 81-87; and Prince et al., 1985, J. Virol. 55: 517-520). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Recent clinical studies have demonstrated the ability of this passively administered RSV hyperimmune globulin (RSV IVIG) to protect at-risk children from severe lower respiratory infection by RSV (See, e.g. Groothius et al., 1993, New Engl. J. Med. 329: 1524-1530; and The PREVENT Study Group, 1997, Pediatrics 99: 93-99). While this is a major advance in preventing RSV infection, this therapy poses certain limitations in its widespread use. First, RSV IVIG must be infused intravenously over several hours to achieve an effective dose. Second, the concentrations of active material in hyperimmune globulins are insufficient to treat adults at risk or most children with comprised cardiopulmonary function. Third, intravenous infusion necessitates monthly hospital visits during the RSV season. Finally, it may prove difficult to select sufficient donors to produce a hyperimmune globulin for RSV to meet the demand for this product. Currently, only approximately 8% of normal donors have RSV neutralizing antibody titers high enough to qualify for the production of hyperimmune globulin.

A humanized antibody directed to an epitope in the A antigenic site of the F protein of RSV, palivizumab, is approved for intramuscular administration to pediatric patients for prevention of serious lower respiratory tract disease caused by RSV at recommended monthly doses of 15 mg/kg of body weight throughout the RSV season (November through April in the northern hemisphere). Palivizumab is a composite of human (95%) and murine (5%) antibody sequences (See, Johnson et al., 1997, J. Infect. Diseases 176: 1215-1224 And U.S. Pat. No. 5,824,307, the entire contents of which are incorporated herein by reference)

Avian & Human Metapneumovirus

Recently, a new member of the Paramyxoviridae family has been isolated from 28 children with clinical symptoms reminiscent of those caused by human respiratory syncytial virus ("hRSV") infection, ranging from mild upper respiratory tract disease to severe bronchiolitis and pneumonia (See, e.g. Van Den Hoogen et al., 2001, Nature Medicine 7: 719-724). The new virus was named human metapneumovirus (hMPV) based on sequence homology and gene constellation. The study further showed that by the age of five years virtually all children in the Netherlands have been exposed to hMPV and that the virus has been circulating in humans for at least half a century.

Avian pneumovirus infection is an emerging disease in the USA despite its presence elsewhere in the world in poultry for many years. In May 1996, a highly contagious respiratory disease of turkeys appeared in Colorado, and an APV was subsequently isolated at the National Veterinary Services Laboratory (NVSL) in Ames, Iowa (See, e.g., Senne et al., 1997, Proc. 134th Ann. Mtg., AVMA, pp. 190). Prior to this time, the United States and Canada were considered free of avian pneumovirus (See, e.g. Pearson et al., 1993, In: Newly Emerging and Re-emerging Avian Diseases Applied Research and Practical Applications for Diagnosis and Control, pp. 78-83; Hecker and Myers, 1993, Vet. Rec. 132: 172). Early in 1997, the presence of APV was detected serologically in turkeys in Minnesota. By the time the first confirmed diagnosis was made, APV infections had already spread to many farms. The disease is associated with clinical signs in the upper respiratory tract: foamy eyes, nasal discharge and swelling of the sinuses. It is exacerbated by secondary infections. Morbidity in infected birds can be as high as 100%. The mortality can range from 1 to 90% and is highest in six to twelve week old poults.

Avian pneumovirus is transmitted by contact. Nasal discharge, movement of affected birds, contaminated water, contaminated equipment; contaminated feed trucks and load-out activities can contribute to the transmission of the virus. Recovered turkeys are thought to be carriers. Because the virus is shown to infect the epithelium of the oviduct of laying turkeys and because APV has been detected in young poults, egg transmission is considered a possibility. Based upon the recent work with hMPV, hMPV likewise appears to be a significant factor in human, particularly, juvenile respiratory disease.

The three above described viruses, RSV, hMPV, and PIV, cause a significant portion of human respiratory disease.

Bacterial Respiratory Infections

Bacterial Pneumonia. There are about 2 million cases of pneumonia each year of which 40,000 to 70,000 result in death (See The Merck Manual of Diagnosis and Therapy (17th ed. 1999). Although certain viruses and fungi cause pneumonia, most cases of pneumonia in adults are caused by bacteria such as *Streptococcus pneumonia, Staphylococcus aureus, Haemophilus influenzae, Chlmayda pneumoniae, C. psittaci, C. trachomatis, Moraxella (Branhamella) catarrhalis, Legionella pneumophila, Klebsiella penumoniae*, and other gram-negative bacilli.

Pneumonia is usually spread by inhaling droplets small enough to reach the alveoli and aspirating secretions from the upper airways. Alcoholics, institutionalized persons, cigarette smokers, patients with heart failure, patients with chronic obstructive airway disease, the elderly, children, infants, infants born prematurely, patients with compromised immune systems, and patients with dysphagia are at greater risk of developing pneumonia.

Pneumonia is diagnosed based on characteristic symptoms and an infiltrate on chest x-ray. Common symptoms of pneumonia include cough, fever, sputum production, tachypnea, and crackles with bronchial breath sounds. Determination of the specific pathogen causing the pneumonia cannot be made in about 30-50% of patients and specimens may be misleading because of normal flora may contaminate samples through the upper airways. Special culture techniques, special stains, serologic assays, or lung biopsies may be used for diagnosis.

Therapies for the treatment of pneumonia consist of respiratory support, such as oxygen, and antibiotics based on determination of the specific bacteria and/or according to the patient's age, epidemiology, host risk factors, and severity of illness. For example, in cases of Staphylococcal pneumonia, anti-bacterial therapy may comprise administration of penicillin (e.g., oxacillin and nafcillin), or cephalosporin (e.g. cephalothin or cefamandol, cefazolin, and cefuroxime). In cases of Streptococcal pneumonia, anti-bacterial therapy may comprise administration of penicillin, cephalosporins, erythromycin, or clindamycin.

The administration of antibiotics may result in side effects, toxicity, and the development of antibiotic resistant strains. In addition, because the pathogen causing pneumonia is difficult to diagnose, the use of antibiotics may be ineffective since both viruses and fungi also cause pneumonia. Thus, new therapies for the treatment of pneumonia are needed.

Tuberculosis. *Mycobacterium tuberculosis* infects 1.9 billion and the active disease, tuberculosis ("TB") results in 1.9 million deaths around the world each year. (See, e.g. Dye et al., 1999, JAMA 282: 677-686). After a century of steadily declining rates of TB cases in the United States, the downward trend was reversed in the late 1980s as a result of the emergence of a multidrug-resistant strain of *M. tuberculosis*, the HIV epidemic, and influx of immigrants. (See, e.g., Navin et al., 2002, Emerg. Infect. Dis. 8:11).

*M. tuberculosis* is an obligate aerobe, nonmotile rod-shaped bacterium. In classic cases of tuberculosis, *M. tuberculosis* complexes are in the well-aerated upper lobes of the lungs. *M. tuberculosis* are classified as acid-fast bacteria due to the impermeability of the cell wall by certain dyes and stains. The cell wall of *M. tuberculosis*, composed of peptidoglycan and complex lipids, is responsible for the bacterium's resistance to many antibiotics, acidic and alkaline compounds, osmotic lysis, and lethal oxidations, and survival inside macrophages.

TB progresses in at least five stages. In the first stage, the subject inhales the droplet nuclei containing less than three bacilli. Although alveolar macrophages take up the *M. tuberculosis*, the macrophages are not activated and do not destroy the bacterium. Seven to 21 days after the initial infection, the *M. tuberculosis* multiplies within the macrophages until the macrophages burst, which attracts additional macrophages to the site of infection that phagocytose the *M. tuberculosis*, but are not activated and thus do not destroy the *M tuberculosis*. In stage 3, lymphocytes, particularly T-cells, are activated and cytokines, including interferon activate macrophages capable of destroying *M. tuberculosis* are produced. At this stage, the patient is tuberculin-positive and a cell mediated immune response, including activated macrophages releasing lytic enzymes and T cell secreting cytokines, is initiated. Although, some macrophages are activated against the *M. tuberculosis*, the bacteria continue to multiply within inactivated macrophages and begin to grow tubercles which are characterized by semi-solid centers. In stage 4, tubercles may invade the bronchus, other parts of the lung, and the blood supply line and the patient may exhibit secondary lesions in other parts of the body, including the genitourinary system, bones, joints, lymph nodes, and peritoneum. In the final stage, the tubercles liquify inducing increased growth of *M. tuberculosis*. The large bacterium load causes the walls of nearby bronchi to rupture and form cavities that enables the infection to spread quickly to other parts of the lung.

Current therapies available for the treatment of TB comprise an initial two month regime of multiple antibiotics, such as rifampcin, isoniazid, pyranzinamide, ethambutol, or streptomycin. In the next four months, only rifampicin and isoniazid are administered to destroy persisting *M. tuberculosis*. Although proper prescription and patient compliance results in a cure in most cases, the number of deaths from TB has been on the rise as a result from the emergence of new *M. tuberculosis* strains resistant to current antibiotic therapies. (See e.g., Rattan et al., 1998, Emerging Infectious Diseases, 4(2): 195-206). In addition, fatal and severe liver injury has been associated with treatment of latent TB with rifampcin and pyranzinamide. (See CDC Morbidity and Mortality Weekly Report, 51(44): 998-999).

Fungal Respiratory Infections. The number of systemic invasive fungal infections rose sharply in the past decade due to the increase in the at-risk patient population as a result of organ transplants, oncology, human immunodeficiency virus, use of vascular catheters, and misuse of broad spectrum antibiotics (See, e.g. Dodds et al., 2000 Pharmacotherapy 20(11): 1335-1355. Seventy percent of fungal-related deaths are caused by *Candida* species, *Aspergillus* species, and *Cryptococcus neoformans*. Yasuda, California Journal of Health-System Pharmacy, May/June 2001, pp. 4-11).

Systemic Candidiasis. 80% of all major systemic fungal infections are due to *Candida* species (See The Merk Manual of Diagnosis and Therapy, 17th ed., 1999). Invasive candidiasis is most often caused by *Candida albicans, Candida troicalis,* and *Candida glabrata* in immunosuppressd patients. Candidiasis is a defining opportunistic infection of AIDS, infecting the esophagus, trachea, bronchi, and lungs. In HIV-infected patients, candidiasis is usually mucocutaneous and infects the oropharynx, the esophagus, and the vagina (See Ampel, April-June 1996, Emerg. Infect. Dis. 2(2): 109-116).

*Candida* species are commensals that colonize the normal GI tract and skin (See The Merk Manual of Diagnosis and Therapy, Berkow et al. (eds.), 17th ed., 1999). Thus, cultures of *Candidia* from sputum, the mouth, urine, stool, vagina, or skin does not necessarily indicate an invasive, progressive infection. In most cases, diagnosis of candidiasis requires presentation of a characteristic clinical lesion, documentation of histopathologic evidence of tissue invasion, or the exclusion of other causes. Symptoms of systemic candidiasis infection of the respiratory tract are typically nonspecific, including dysphagia, coughing, and fever.

All forms of candidiasis are considered serious, progressive, and potentially fatal. Therapies for the treatment of candidiasis typically include the administration of the combination of the anti-fungal agents amphotericin B and flucytosine. Unfortunately, acute renal failure has been associated with amphotericin B therapy. Fluconazole is not as effective as amphotericin B in treating certain species of *Candida*, but is useful as initial therapy in high oral or intravenous doses while species identification is pending (See The Merk Manual of Diagnosis and Therapy, 17th ed., 1999). Fluconazole, however, has led to increasing treatment failures and anti-fungal resistance. Ampel, supra. Thus, there is a need for novel therapies of systemic candidiasis.

Aspergillosis. *Aspergillus* includes 132 species and 18 variants among which *Aspergillus fumigatus* is involved in 80% of *Aspergillus*-related diseases. *Aspergillus fumigatus* is the most common cause of invasive pulmonary aspergillosis that extends rapidly, causing progressive, and ultimately fatal respiratory failure (See The Merk Manual of Diagnosis and Therapy, 17th ed., 199). Patients undergoing long-term high-dose corticosteroid therapy, organ transplant patients, patients with hereditary disorders of neutrophil function, and patients infected with AIDS are at risk for aspergillosis.

Clinical manifestations of invasive pulmonary infection by *Aspergillus* include fever, cough, and chest pain. *Aspergillus* colonizes preexisting cavity pulmonary lesions in the form of aspergilloma (fungus ball), which is composed of tangled masses of hyphae, fibrin exudate, and inflammatory cells encapsulated by fibrous tissue. Aspergillomas usually form and enlarge in pulmonary cavities originally caused by bronchiectasis, neoplasm, TB, and other chronic pulmonary infections. Most aspergillomas do not respond to or require systemic anti-fungal therapy. However, invasive infections often progress rapidly and are fatal, thus aggressive therapy comprising IV amphotericin B or oral itraconazole is required. Unfortunately, high-dose amphotericin B may cause renal failure and itraconazole is effective only in moderately severe cases. Therefore, there is a need for new therapies for the treatment of aspergillosis.

Cryptococcosis. Cases of cryptococcosis were rare before the HIV epidemic. AIDS patients, patients with Hodgkin's or other lymphomas or sarcoidosis, and patients undergoing long-term corticosteroid therapy are at increased risk for cryptococcosis. In most cases, cryptococcal infections are self-limited, but AIDS-associated cryptococcal infection may be in the form of a severe, progressive pneumonia with acute dyspnea and primary lesions in the lungs. In cases of progressive disseminated cryptococcosis affecting non-immunocompromised patients, chronic meningitis is most common without clinically evident pulmonary lesions.

Immunocompetent patients do not always require the administration of a therapy to treat localized pulmonary cryptococcosis. However, when such patients are administered a therapy for the treatment of localized pulmonary cryptococcosis, it typically comprises of administration of amphotericin B with or without flucytosine. AIDS patients are generally administered an initial therapy comprising amphotericin B and flucytosine and then oral fluconazole thereafter to treat cryptococcosis. Renal and hematologic function of all patients receiving amphotericin B with or without flucytosine must be evaluated before and during therapy since flucytosine blood levels must be monitored to limit toxicity and administration of flucytosine may not be safe for patients with preexisting renal failure or bone marrow dysfunction. Thus, new therapies for the treatment of cryptococcosis are needed.

Thus, current therapies for respiratory infections involve the administration of anti-viral agents, anti-bacterial, and anti-fungal agents for the treatment, prevention, or amelioration of viral, bacterial, and fungal respiratory infections, respectively. Unfortunately, in regard to certain infections, there are no therapies available, infections have been proven to be refractory to therapies, or the occurrence of side effects outweighs the benefits of the administration of a therapy to a subject. The use of anti-bacterial agents for treatment of bacterial respiratory infections may also produce side effects or result in resistant bacterial strains. The administration of anti-fungal agents may cause renal failure or bone marrow dysfunction and may not be effective against fungal infection in patients with suppressed immune systems. Additionally, the infection causing microorganism (e.g., virus, bacterium, or fungus) may be resistant or develop resistance to the administered therapeutic agent or combination of therapeutic agents. In fact, microorganisms that develop resistance to administered therapeutic agents often develop pleiotropic drug or multidrug resistance, that is, resistance to therapeutic agents that act by mechanisms different from the mechanisms of the administered agents. Thus, as a result of drug resistance, many infections prove refractory to a wide array of standard treatment protocols. Therefore, new therapies for the treatment, prevention, management, and/or amelioration of respiratory infections and symptoms thereof are needed.

In addition, a need exists for compositions and methods for the treatment of respiratory infection (e.g., in CF patients as well as other classes of subjects susceptible to respiratory infection described herein). Such a composition would ideally be formulated without contaminants (e.g., capable of generating unwanted side effects) and would be effective in a relatively short time frame to treat and/or prevent infection.

Accordingly, in some embodiments, the present invention provides a composition comprising a nanoemulsion, and methods of pulmonary administration of the same to prevent and/or treat respiratory infection. In some embodiments, the nanoemulsion comprises ethylenediaminetetraacetic acid (EDTA). The present invention is not limited by the amount of EDTA utilized. In some embodiments, 0.01-0.1 mM, 0.1-1.0 mM, 1.0-1.5 mM, 1.5-2.5 mM, 2.5-5.0 mM, 5.0-10.0 mM, 10-20 mM, 20-30 mM, or 30-50 mM EDTA is used. However, the present invention is not limited to this amount of EDTA. In some embodiments, less than 0.01 mM or more than 50 mM EDTA is utilized. In some embodiments, the composition is co-administered with a hypertonic salt (e.g., sodium chloride) solution (e.g., a 6-7%, 1-3%, 3-6%, 0.1-1%, or more than 7% salt solution (e.g., NaCl solution)). In some embodiments, the composition comprises a 20% nanoemulsion solution. In some embodiments, the composition comprises greater than 20% (e.g., 25%, 30%, or more) nanoemulsion solution. In some embodiments, the composition comprises less than 20% (e.g., 15%, 10% or less) nanoemulsion solution. However, the present invention is not limited to this amount (e.g., percentage) of nanoemulsion. For example, in some embodiments, a composition comprises less than 10% nanoemulsion. In some embodiments, a composition comprises more than 20% nanoemulsion. In some embodiments, the composition comprises 10 mM EDTA. In some embodiments, the composition comprises 20 mM EDTA. In some embodiments, a composition of the present invention comprises any of the nanoemulsions described herein. In some embodiments, a composition comprising a nanoemulsion utilized to treat bacteria (e.g., present in pulmonary space of a subject (e.g., biofilm forming bacteria)) comprises $P_{407}5EC$. In some embodiments, a composition comprising a nanoemulsion comprises $W_{80}5EC$.

Administration of nanoemulsion alone or in combination with EDTA (e.g., 10-20 mM EDTA) was able to achieve complete killing of $10^6$ bacteria in PBS in 60 minutes (See Examples 2-4). In the presence of hypertonic saline (e.g., 6-7% NaCl), the killing ability of the nanoemulsion was surprisingly and strikingly enhanced, achieving complete killing within 15 minutes while in the presence of 20 mM EDTA (See Example 2). Also, nanoemulsions comprising a lower concentration of EDTA were able to achieve complete killing of bacteria in 30 minutes in the presence of hypertonic saline.

Thus, in some embodiments, the present invention provides that a nanoemulsion composition can be used to kill (e.g., completely) bacteria over a short time period (e.g., less than 60 minutes, less than 30 minutes, or less than 15 minutes).

The present invention also demonstrates that compositions of the present invention are able to eradicate a mixed population of bacteria. Moreover, toxicity studies performed during the development of embodiments of the present invention characterized the nanoemulsion compositions as being safe and causing no detectable harm to a subject (e.g., no histological changes and/or detectable pathology (See, e.g., Example 1)).

As described in Examples 3 and 4, compositions comprising nanoemulsions of the present invention are able to treat (e.g., kill and/or inhibit growth of) bacterial species that are generally not virulent in healthy persons, but that are opportunists that cause severe and chronic respiratory tract infections (e.g., in individuals with cystic fibrosis (CF)). Unremitting infection with these species results in inflammation and progressive lung disease that culminates in pulmonary failure, the leading cause of death for CF patients. Effective therapy of pulmonary infection in CF to date has been severely limited by the broad spectrum antimicrobial resistance exhibited by these species, which are among the most drug-resistant bacteria encountered in human infection. The site of infection in CF presents another important obstacle to effective therapy. Infecting bacteria primarily reside within the airway lumen in sputum, airway epithelial surface fluid, and the bronchial mucosa (ref). The penetration of systemically delivered antimicrobials to this infected site is generally poor. Treatment is further hampered by bacterial biofilm formation, which is believed to occur in the airways of infected patients, and by the exceptionally viscous secretions that characterize the CF respiratory tract.

Although an understanding of a mechanism is not necessary to practice the present invention, and the present invention is not limited to any particular mechanism of action, in some embodiments, a mechanism of bacterial and/or viral killing utilizing compositions comprising nanoemulsions of the present invention involves fusion of the emulsion with microorganism lipid membranes, leading to rapid osmotic disruption and cell lysis (See, e.g., Hamouda and Baker, J Appl Microbiol. 2000 September; 89(3):397-403). Additionally, in some embodiments, electrostatic attraction (e.g., provided by cationic surface charge of CPC) overcomes the LPS-mediated resistance of gram-negative bacteria to neutral and anionic detergents (See, e.g., Hamouda and Baker, J Appl Microbiol. 2000 September; 89(3):397-403). In some embodiments, bactericidal activity of a composition comprising a nanoemulsion (e.g., $P_{407}5EC$ (e.g., against gram-negative and/or gram-positive bacteria)) is enhanced by the addition of EDTA. Although an understanding of a mechanism is not necessary to practice the present invention, and the present invention is not limited to any particular mechanism of action, in some embodiments, EDTA chelates divalent cations that stabilize outer membrane LPS thereby facilitating interactions with the cationic emulsion, an interaction that leads to membrane permeabilization and lysis as well as augmenting transmembrane diffusion of macromolecules (See, e.g., Rabinovich-Guilatt et al., J Drug Target. 2004; 12(9-10):623-33, Vaara, Microbiol Rev. 1992 September; 56(3):395-411).

Experiments conducted during development of embodiments of the present invention identified $P_{407}5EC$ to be stable after nebulization in 7% saline using the PARI LC Plus nebulizer. Inhalation of a single dose of $P_{407}$5EC nebulized in 7% saline was well tolerated by animals. Thus, in some embodiments, the present invention provides compositions comprising $P_{407}$5EC and hypertonic saline, and methods of using the same (e.g., via inhalation (e.g., post nebulizing the solution)) for treating one or more types of pulmonary bacterial infections (e.g., to treat bacteria and/or bacterial biofilms (e.g., that possess resistance to conventional treatments) without increasing the already high treatment burden for CF patients).

For example, experiments conducted during development of embodiments of the invention show that compositions comprising nanoemulsions (e.g., $P_{407}$5EC and saline solution) were effective to treat (e.g., kill and/or inhibit growth of) species within the *Burkholderia cepacia* complex (Bcc) (See, e.g., Example 3). Infection with *Burkholderia cepacia* species is particularly refractory to antimicrobial therapy and associated with increased rates of morbidity and mortality in CF. Infection with Bcc is also regarded by many CF care centers as an absolute contraindication to lung transplantation. Compositions comprising nanoemulsions (e.g., $P_{407}$5EC and saline solution) were effective to treat (e.g., kill and/or inhibit growth of) *B. multivorans* and *B. cenocepacia* which account for the majority of Bcc infection in CF (See, e.g., Reik J Clin Microbiol. 2005 June; 43(6):2926-8). Compositions comprising nanoemulsions (e.g., $P_{407}$5EC and saline solution) were effective to treat (e.g., kill and/or inhibit growth of) B. gladioli, which although not a member of the Bcc, is being recovered with increasing frequency from CF patients. Also shown in Example 3, compositions comprising nanoemulsions (e.g., $P_{407}$5EC) were effective to treat (e.g., kill and/or inhibit growth of) *Acinetobacter*, which although currently infrequently recovered in CF, appears to be an emerging pathogen in this patient population. The great majority (94%) of isolates tested in Example 3 were recovered from cultures of respiratory specimens from persons with CF. The panel also included one representative isolate from each of five previously described so-called epidemic lineages, each of which has been identified as infecting multiple CF patients. These included the *B. cenocepacia* ET12 (Johnson et al., *J Clin Microbiol* 1994; 32:924-30), PHDC (Chen et al., *J Pediatr* 2001; 139:643-9), and Midwest (Coenye and LiPuma, J. Infect. Dis. 185:1454-1462) lineages, as well as the *B. multivorans* OHBM lineage (Biddick et al., *FEMS Microbiol Lett* 2003; 228:57-62) and the *B. dolosa* SLC6 lineage (Biddick et al., *FEMS Microbiol Lett* 2003; 228:57-62). Compositions comprising nanoemulsions (e.g., $P_{407}$5EC and saline solution) effectively treated (e.g., killed and/or inhibited growth of) each of these different species. Moreover, compositions comprising nanoemulsions (e.g., $P_{407}$5EC) were effective to treat (e.g., kill and/or inhibit growth of) strains that were found in previous susceptibility testing to be multi-drug resistant (e.g., defined as resistant to all antibiotics tested in two of three antibiotic classes: lactams (including carbapenems), aminoglycosides, and quinolones) as well as panresistant strains (See Example 3). Genotyping analyses of all isolates was performed to confirm that each sample treated was a distinct strain.

As shown in Example 3, $P_{407}$5EC showed very good activity against the strains tested. With the exception of two *B. cenocepacia* strains, all strains in the test panel were inhibited by a $P_{407}$5EC concentration of ≤125 μg/ml, or a 1:16 dilution of the starting material; 59% of strains were inhibited by a concentration of ≤31.2 μg/ml, a 1:64 dilution of $P_{407}$5EC. Multi-drug resistant or panresistant strains did not show decreased susceptibility to $P_{407}$5EC, demonstrating $MIC_{90}$s of 125 μg/ml and 62.5 μg/ml, respectively. In general, *Burkholderia* species tended to be slightly less susceptible to $P_{407}$5EC than the other species examined. Sixteen of the 18 strains requiring the highest MICs were *Burkholderia*. Conversely, 33 of the 38 strains with the lowest tested MIC (15.6 μg/ml) were non-*Burkholderia* species. No striking differences in $P_{407}$5EC activity was observed among the 10 *Burkholderia* species examined, although the two strains requiring the highest MICs (250 μg/ml and 500 μg/ml) were both *B. cenocepacia*. Among the non-*Burkholderia* species, Ralstonia strains were most susceptible ($MIC_{90}$≤15.6 μg/ml) while *Acinetobacter* strains were relatively less susceptible ($MIC_{90}$=125 μg/ml). No evidence was found of tolerance to $P_{407}$5EC among a subset of 34 strains for which both MIC and MBC were determined. $P_{407}$5EC killing of planktonically grown bacteria was time- and concentration-dependent; at a concentration 16 times greater than the MIC, complete killing was achieved within 30 min. Thus, the present invention provides that relatively brief exposure of bacteria to $P_{407}$5EC can be utilized to effect several log decreases in viable bacteria. Thus, a composition comprising a nanoemulsion (e.g., $P_{407}$5EC) of the present invention can be utilized individually, or in combination with other antimicrobials, to kill and/or inhibit growth of bacteria.

A great deal of attention has been paid recently to the role of biofilm formation in respiratory tract infection in CF. Several species involved in CF infection, including *P. aeruginosa* and *Burkholderia*, have the capacity to produce biofilms in vitro, and emerging evidence strongly suggests that biofilm formation within the airways of infected patients contributes to disease progression and persistence of infection (See, e.g., Favre-Bonte et al., Microb Pathog. 2002 March; 32(3):143-7); Schwab et al., Infect Immun. 2002 August; 70(8):4547-55; Singh et al., Nature. 2000 Oct. 12; 407(6805):762-4). Sessile bacteria within biofilms demonstrate increased antimicrobial resistance relative to their planktonic counterparts (Stewart and Costerton, Lancet. 2001 Jul. 14; 358(9276):135-8; Desai et al., J Antimicrob Chemother. 1998 August; 42(2): 153-60; Moskowitz et al., J Clin Microbiol. 2004 May; 42(5): 1915-22; Caraher et al. Eur J Clin Microbiol Infect Dis. 2007 March; 26(3):213-6).

Thus, experiments were conducted during development of embodiments of the invention to assess the activity of $P_{407}5EC$ against bacteria grown in vitro as biofilms. A relatively strict definition of in vitro biofilm formation was employed, as described in Example 3, in an effort to provide a stringent test of $P_{407}5EC$ activity. 12 strains that met the definition were tested. As shown in Example 3, the strains represented several species and a range of susceptibility to $P_{407}5EC$ based on standard MIC/MBC testing. Although the MBIC and MBEC of $P_{407}5EC$ were increased compared to the respective MIC and MBC for each strain tested (median four-fold increase in MBIC compared to MIC), all 12 strains were inhibited or killed by $P_{407}5EC$ when grown as biofilms. Only a single strain required undiluted $P_{407}5EC$ (2000 µg/ml) for eradication of viable biofilm bacteria. Relative biomass was assessed among the biofilm forming strains spectrophotometrically with crystal violet staining and no correlation was observed between biomass and MBIC/MBEC. In fact, although *B. gladioli* strain AU10529 produced the greatest biomass among the 12 strains tested, the MBIC and MBEC of $P_{407}5EC$ for this strain were relatively low (both 62.5 µg/ml). Conversely, *B. cenocepacia* strain J2315 produced relatively little biomass, yet required a $P_{407}5EC$ MBEC of 1000 µg/ml.

Figure 10:
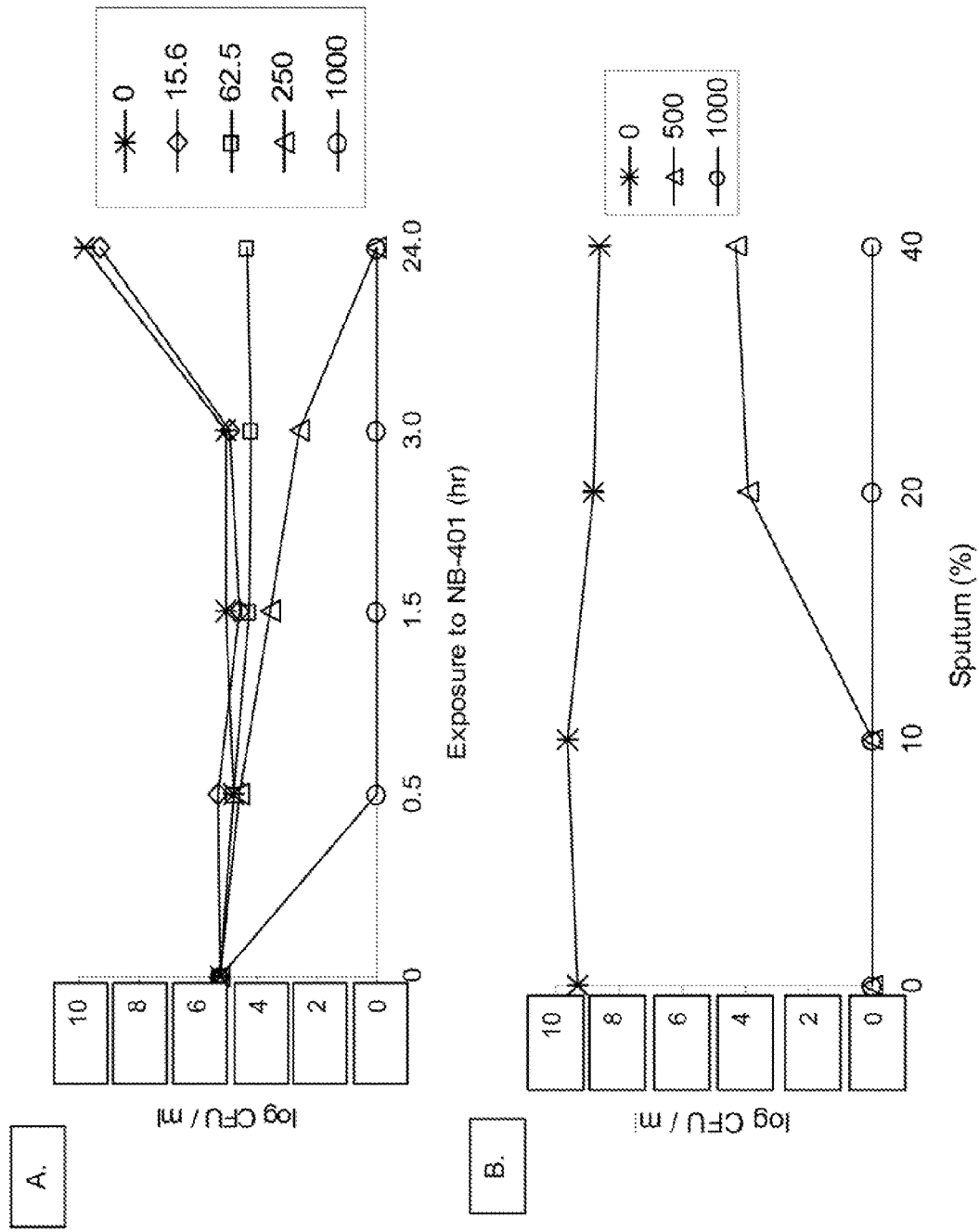

CF sputum, like biofilm, is reported to antagonize the activity of antibacterial drugs (See, e.g., Hunt et al., Antimicrob Agents Chemother. 1995 January; 39(1):34-9). Glycoproteins such as mucin, which compose 2-3% of the dry weight of sputum, and high molecular weight DNA are present in elevated levels resulting in exceptionally viscous sputum that provides a physical barrier protecting bacteria. In addition, these macromolecules bind and sequester antibiotics while small cationic molecules and the decreased pH of CF sputum block drug penetration into bacteria and reduce drug bioactivity. The strategy of increasing drug dosing to overcome these obstacles is limited by drug toxicity. To assess the impact of sputum on the antibacterial activity of $P_{407}5EC$, standard planktonic susceptibility testing was repeated for the 12 biofilm-forming strains in the presence of CF sputum. A mixture of sputum from 15 CF patients was used to avoid inter-patient variation in macromolecule and high molecular weight DNA composition, and ionic conditions, and only mechanical shearing was applied to minimize changes to the native microenvironment (See, e.g., Grebski et al., Chest. 2001 May; 119(5):1521-5). The activity of $P_{407}5EC$ against bacteria suspended in media containing 43% sputum (the maximum sputum concentration achieved in the test system) was decreased with bactericidal concentrations 2- to 32-fold greater than the respective planktonic MBCs without sputum. The sputum-MBCs were identical to (6 of 12) or within one dilution of (6 of 12) the MBECs obtained with biofilm grown bacteria. Although the activity of $P_{407}5EC$ was similarly antagonized by both CF sputum and biofilm growth, it remained bactericidal for all the strains tested under both test conditions (See FIG. 10).

Thus, in some embodiments, the present invention provides compositions comprising nanoemulsions (e.g., $P_{407}5EC$) and methods of using the same for antimicrobial treatment for infection due to CF-related opportunistic pathogens. In particular, nanoemulsion compositions of the present invention are rapidly bactericidal, and active against bacteria whether grown planktonically or as a biofilm, or in the presence of CF sputum. Moreover, compositions comprising nanoemulsions of the present invention are exceptionally stable, unchanged after nebulization, and broadly microbicidal. Importantly, the development of resistance to a nanoemulsion composition of the present invention has not been observed by any bacterial species examined to date. Thus, the present invention provides that $P_{407}5EC$ can be used effectively as an inhaled antimicrobial.

The present invention is not limited to treatment of bacterial biofilms the reside in pulmonary spaces (e.g., within a subject with CF). Indeed, compositions comprising a nanoemulsion of the present invention can be utilized as a therapeutic and/or antimicrobial agent (e.g., to kill and/or inhibit growth of) bacterial biofilms in any clinical and/or industrial setting.

Multiple species of bacteria exist that are able to form biofilms. For example, bacteria that adhere to implanted medical devices or damaged tissue often encase themselves in a hydrated matrix of polysaccharide and protein to form biofilm. Biofilms pose a serious problem for public health because of the increased resistance of biofilm-associated organisms to antimicrobial agents and the association of infections with these organisms in patients with indwelling medical devices or damaged tissue. Antibiotic resistance of bacteria growing in biofilms contributes to the persistence and chronic nature of infections such as those associated with implanted medical devices. The mechanisms of resistance in biofilms are different from the now familiar plasmids, transposons, and mutations that confer innate resistance to individual bacterial cells. In biofilms, resistance seems to depend on multicellular strategies.

Biofilms are complex communities of microorganisms attached to surfaces or associated with interfaces or damaged tissue. Despite the focus of modern microbiology research on pure culture, planktonic (free-swimming) bacteria, it is now widely recognized that most bacteria found in natural, clinical, and industrial settings persist in association with surfaces as biofilms. Furthermore, these microbial communities are often composed of multiple species that interact with each other and their environment. The determination of biofilm architecture, particularly the spatial arrangement of microcolonies (clusters of cells) relative to one another, has profound implications for the function of these complex communities.

The biofilm matrix is a dynamic environment in which the component microbial cells appear to reach homeostasis and are optimally organized to make use of all available nutrients. The matrix therefore shows great microheterogeneity, within which numerous microenvironments can exist. Biofilm formation is believed to be a two-step process in which the attachment of bacterial cells to a surface is followed by growth dependent accumulation of bacteria in multilayered cell clusters. Although exopolysaccharides provide the matrix framework, a wide range of enzyme activities can be found within the biofilm, some of which greatly affect structural integrity and stability.

More specifically, during the first phase of formation, it is hypothesized that the fibrinogen and fibronectin of host plasma cover the surface of a medical implant or damaged tissue and are identified by constitutively expressed microbial surface components, which mediate the initial attachment of bacteria to the surface of the biomaterial or damaged tissue. In the second step, a specific gene locus in the bacteria cells, called the intracellular adhesion (ica) locus, activates the adhesion of bacteria cells to each other, forming the secondary layers of the biofilm. The ica locus is responsible for the expression of the capsular polysaccharide operon, which in turn activates polysaccharide intercellular adhesion (PIA), via the sugar poly-N-succinylglucosamine (PNSG), a-1,6-linked glucosaminoglycan. The production of this polysaccharide layer gives the biofilm its slimy appearance when viewed using electron microscopy.

Staphylococcus aureus is a highly virulent human pathogen. Both *S. aureus* and coagulase-negative staphylococci have emerged as major nosocomial pathogens associated with biofilm formation on implanted medical devices and damaged tissue. These organisms are among the normal carriage flora of human skin and mucous membranes, making them prevalent complications during and after invasive surgery or prolonged hospital stays. As bacteria carried on both healthy and sick people, staphylococci are considered opportunistic pathogens that invade patients via open wounds and via biomaterial implants.

Biofilm infections associated with *S. aureus* are a significant cause of morbidity and mortality, particularly in settings such as hospitals, nursing homes and infirmaries. Patients at risk include infants, the elderly, the immuno-compromised, the immuno-suppressed, and those with chronic conditions requiring frequent hospital stays. Patients with intravascular and other implanted prosthetic devices are at even greater risk from staphylococcal infections because of compromised immune systems and the introduction of foreign bodies, which serve to damage tissue and/or act as a surface for the formation of biofilms. Such infections can have chronic, if not fatal, implications.

Catheter related infections continue to be a significant source of morbidity and mortality in patients requiring catheterization. The reported incidence in the United States is 4%, which equates to 200,000 patients per year. Additionally, catheter related infections have an attributable mortality of 14-24% and increase medical expenses by prolonging hospitalization. As a result, prevention or even reduction in the incidence of these catheter-related infections could have a significant healthcare benefit.

Catheter infections are most commonly caused by staphylococci, either coagulase negative staphylococci (CoNS) or *S. aureus*. Infections caused by CoNS can be mild and some can be treated by either removing the catheter or a course of antibiotics with the catheter in place. *S. aureus* infections are usually more severe and require removal of the catheter or other prosthetic device in addition to extended antibiotic therapy.

*S. aureus* is a prodigious toxin producer and a highly virulent human pathogen. It is the cause of a variety of human diseases, ranging from localized skin infections to life-threatening bacteremia and infections of vital organs. If not rapidly controlled, a *S. aureus* infection can spread quickly from the initial site of infection to other organs. Although the foci of infection may not be obvious, organs particularly susceptible to infection include the heart valves, kidneys, lungs, bones, meninges and the skin of burn patients.

The causes of biofilm resistance to antibiotics include the failure of some antimicrobial agents to penetrate all the layers of a biofilm, the slow-growth rate of certain biofilm cells that make them less susceptible to antimicrobial agents requiring active bacterial growth, and the expression of gene patterns by the bacterial cells embedded in the biofilm that differ from the genes expressed in their planktonic (free-swimming) state. These differences in biofilm-associated bacteria render antimicrobial agents that work effectively to kill planktonic bacteria ineffective in killing biofilm-associated bacteria. Often the only way to treat biofilms (e.g., associated with catheters or prosthetic devices) is the removal of the contaminated device, which may require additional surgery and present further risks to patients.

Thus, as used herein, biofilms refer to an aggregate of microorganisms with an extracellular matrix that facilitates adhesion to, and colonization and growth of the aggregate on a surface, such as an internal or external tissue or organ. Biofilms can be comprised of bacteria, fungi, yeast, protozoa, or other microorganisms. Bacterial biofilms typically display high resistance to antibiotics, often up to 1,000-times greater resistance than the same bacteria not growing in a biofilm.

In some embodiments, compositions and methods of the invention are utilized to treat (e.g., kill and/or inhibit growth of) and/or prevent biofilms on and/or within a subject (e.g., within the pulmonary system, on internal organs or tissue (e.g., the bladder, kidney, heart, middle ear, sinuses, a joint, the eye), on an external tissue (e.g., the skin), and/or oral surfaces such as teeth, tongue, oral mucosa, or gums. Compositions and methods of the invention may be used to treat a biofilm-associated condition such as a soft-tissue infection, chronic sinusitis, endocarditis, osteomyelitis, urinary tract infection, chronic bacterial vaginosis, dental plaque or halitosis, infection of prosthetic device and/or catheter, bacterial keratitis, or prostatitis.

As described in Examples 3 and 4, compositions of the present invention can be utilized to treat (e.g., kill and/or inhibit growth of) any one or more Gram-positive and Gram-negative bacterial species. Indeed, compositions and methods of the present invention can be utilized to kill and/or inhibit growth of a number of bacterial species including, but not limited to, *Staphylococcus aureus*, coagulase negative staphylococci such as *Staphylococcus epidermis, Streptococcus pyogenes* (Group A), *Streptococcus* species (viridans group), *Streptococcus agalactiae* (group B), *S. bovis, Streptococcus* (anaerobic species), *Streptococcus pneumoniae, Enterococcus species, Bacillus anthracis, Corynebacterium diptheriae,* and *Corynebacterium* species which are diptheroids (aerobic and anaerobic), *Listeria monocytogenes, Clostridium tetani,* and *Clostridium difficile, Escherichia coli, Enterobacter species, Proteus mirablis, Pseudomonas aeruginosa, Klebsiella pneumoniae, Salmonella, Shigella, Serratia, Campylobacter jejuni, Neisseria, Branhamella catarrhalis,* and *Pasteurella.*

Compositions and methods of the present invention can be utilized to treat (e.g., kill and/or inhibit growth of) organisms capable of forming biofilms including, but not limited to, dermatophytes (e.g., Microsporum species such as *Microsporum canis, Trichophyton* species such as *Trichophyton rubrum* and *Trichophyton mentagrophytes*), yeasts (e.g., *Candida albicans, Candidaparapsilosis, Candida glabrata, Candida tropicalis,* and other *Candida* species including drug resistant *Candida* species), Epidermophytonfloccosum, Malasseziafuurfur (*Pityropsporon orbiculare, Pityropsporon ovale*) *Cryptococcus neoformans, Aspergillusfumigatus* and other *Aspergillus* species, Zygomycetes (Rizopus, *Mucor*), hyalohyphomycosis (*Fusarium* species), *Paracoccidiodes brasiliensis, Blastmyces dermatitides, Histoplasma capsulatum, Coccidiodes immitis, Sporothrix schenckii,* and *Blastomyces.*

Thus, in some embodiments, the present invention provides a method for treating a subject possessing a biofilm (e.g., possessing an indwelling prosthetic device or catheter, wherein the indwelling prosthetic device or catheter is in contact with a biofilm, or wherein the subject has an infection (e.g., respiratory infection) within which a biofilm resides) comprising administering to the subject a composition comprising a nanoemulsion (e.g., $P_{407}5EC$) under conditions such that the biofilm is altered and/or bacteria residing within the biofilm are killed and/or their growth is inhibited. In some embodiments, altering the biofilm comprises eradicating the biofilm. In some embodiments, altering the biofilm comprises killing bacteria involved in forming the biofilm. In some embodiments, the bacteria comprise S. aureus, S. epidermidis, antibiotic resistant bacteria (e.g., methicillin resistant, vancomycin resistant, etc.), and/or other type of bacteria described herein. In some embodiments, the composition comprising a nanoemulsion (e.g., $P_{407}5EC$) is co-administered with one or more antibacterial agents. In some embodiments, the antibacterial agents are selected from the group comprising, but not limited to, antibiotics, antibodies, antibacterial enzymes, peptides, and lanthione-containing molecules. In some embodiments, the antibiotic interferes with or inhibits cell wall synthesis. In some embodiments, the antibiotic is selected from the group including, but not limited to, β-lactams, cephalosporins, glycopeptides, aminoglycosides, sulfonomides, macrolides, folates, polypeptides and combinations thereof. In some embodiments, the antibiotic interferes with protein synthesis (e.g., glycosides, tetracyclines and streptogramins). The present invention is not limited by the number of doses of composition comprising nanoemulsion administered. In some embodiments, multiple doses are administered on separate days. In some embodiments, the multiple doses are administered on the same day. In some embodiments, a composition comprising a nanoemulsion described herein is administered continuously. In some embodiments, co-administration with a composition comprising a nanoemulsion permits administering a lower dose of an antibacterial agent than would be administered without co-administration of a composition comprising a nanoemulsion. In some embodiments, the composition comprising a nanoemulsion described herein is administered using a nebulizer. In some embodiments, administration is intramuscularly, subcutaneously, locally, directly into an infected site, directly onto an indwelling prosthetic device (e.g., a shunt, stent, scaffold for tissue construction, feeding tube, punctual plug, artificial joint, pacemaker, artificial valve, etc.) or catheter. In some embodiments, administration is directly through a catheter.

The present invention is not limited by the type of microbe treated. Indeed a variety of microbial pathogens can be treated (e.g., killed (e.g., completely killed)) and/or the growth thereof prevented and/or attenuated in a subject using the compositions and methods of the present invention including, but not limited to, bacteria, viruses, and fungi described herein.

The present invention also provides compositions and methods for treating (e.g., killing and/or inhibiting growth of) organisms that heretofore display resistance to a broad spectrum of antibiotics (e.g., species of the genus Acinetobacter).

Acinetobacter species are generally considered nonpathogenic to healthy individuals. However, several species persist in hospital environments and cause severe, life-threatening infections in compromised patients (See, e.g., Gerischer U (editor). (2008). Acinetobacter Molecular Biology, 1st ed., Caister Academic Press). The spectrum of antibiotic resistances of these organisms together with their survival capabilities make them a threat to hospitals as documented by recurring outbreaks both in highly developed countries and elsewhere. Infections occur in immunocompromised individuals, and the strain A. baumannii is the second most commonly isolated nonfermenting bacteria in human specimens. Acinetobacter is frequently isolated in nosocomial infections and is especially prevalent in intensive care units, where both sporadic cases as well as epidemic and endemic occurrence is common. A. baumannii is a frequent cause of nosocomial pneumonia, especially of late-onset ventilator associated pneumonia. It can cause various other infections including skin and wound infections, bacteremia, and meningitis. A. lwoffi is also causative of meningitis. A. baumannii can survive on the human skin or dry surfaces for weeks.

Since the start of the Iraq War, over 700 U.S. soldiers have been infected or colonized by A. baumannii. Four civilians undergoing treatment for serious illnesses at Walter Reed Army Medical Center in Washington, D.C., contracted A. baumannii infections and died. At Landstuhl Regional Medical Center, a U.S. military hospital in Germany, another civilian under treatment, a 63-year-old German woman, contracted the same strain of A. baumannii infecting troops in the facility and also died.

Acinetobacter species are innately resistant to many classes of antibiotics, including penicillin, chloramphenicol, and often aminoglycosides. Resistance to fluoroquinolones has been reported during therapy and this has also resulted in increased resistance to other drug classes mediated through active drug efflux. A dramatic increase in antibiotic resistance in Acinetobacter strains has been reported by the CDC and the carbapenems are recognised as the gold-standard and/or treatment of last resort. An increase in resistance to the carbapenems leaves very little treatment option although there has been some success reported with polymyxin B. Acinetobacter species are unusual in that they are sensitive to sulbactam; sulbactam is most commonly used to inhibit bacterial beta-lactamase, but this is an example of the antibacterial property of sulbactam itself.

Thus, in some embodiments, compositions and methods of the present invention are utilized to treat (e.g., kill and/or inhibit growth of) bacteria of the Acinetobacter species (e.g., individually or in combination with other treatments (e.g., carbapenems, polymyxin B, and/or sulbactam)).

The present invention is not limited by the type of nanoemulsion utilized (e.g., for respiratory administration). Indeed, a variety of nanoemulsion compositions are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweetners, bulking agents, and the like) and pharmaceutically acceptable compounds. Certain exemplary embodiments of the various compounds contemplated for use in the compositions of the present invention are presented below. Unless described otherwise, nanoemulsions are described in undiluted form.

A. Aqueous Phase

In certain preferred embodiments, a nanoemulsion comprises about 5 to 60, preferably 10 to 40, more preferably 15 to 30, vol. % aqueous phase, based on the total volume of the emulsion, although higher and lower amounts are contemplated. In preferred embodiments, the aqueous phase comprises water at a pH of about 4 to 10, preferably about 6 to 8. When the emulsions of the present invention contain a germination enhancer, the pH is preferably 6 to 8. The water is preferably deionized (hereinafter "DiH$_2$O") or distilled. In some embodiments the aqueous phase comprises phosphate buffered saline (PBS). In those embodiments of the present invention intended for administration to, or contact with, a subject (e.g., a subject vaccinated with a composition of the present invention), the aqueous phase, and any additional compounds provided in the aqueous phase, may further be sterile and pyrogen free.

B. Oil Phase and Solvents

In certain preferred embodiments, the oil phase (e.g., carrier oil) of a nanoemulsion comprises 30-90, preferably 60-80, and more preferably 60-70, vol. % of oil, based on the total volume of the emulsion, although higher and lower amounts are contemplated. Suitable oils include, but are not limited to, soybean oil, avocado oil, flaxseed oil, coconut oil, cottonseed oil, squalene oil, olive oil, canola oil, corn oil, rapeseed oil, safflower oil, sunflower oil, pine oil (e.g., 15%), Olestra oil, fish oils, flavor oils, water insoluble vitamins and mixtures thereof. In particularly preferred embodiments, soybean oil is used. Additional contemplated oils include motor oils, mineral oils, and butter. In preferred embodiments of the present invention, the oil phase is preferably distributed throughout the aqueous phase as droplets having a mean particle size in the range from about 1-2 microns, more preferably from 0.2 to 0.8, and most preferably about 0.8 microns. In other embodiments, the aqueous phase can be distributed in the oil phase. In some preferred embodiments, very small droplet sizes are utilized (e.g., less than 0.5 microns) to produce stable nanoemulsion compositions. It is contemplated that small droplet compositions also provide clear solutions, which may find desired use in certain product types.

In some embodiments, the oil phase comprises 3-15, preferably 5-10 vol. % of an organic solvent, based on the total volume of the emulsion, although higher and lower amounts are contemplated. Although an understanding of the mechanism is not necessary to practice the present invention and the present invention is not limited to any particular mechanism of action, it is contemplated that the organic phosphate-based solvents employed in an emulsion serves to disrupt and inactivate the pathogen (e.g., disrupt lipids in membranes or viral envelopes). Thus, any solvent that can remove sterols or phospholipids finds use in the emulsions of the present invention. Suitable organic solvents include, but are not limited to, organic phosphate based solvents or alcohols. In preferred embodiments, the organic phosphate based solvents include, but are not limited to, dialkyl- and trialkyl phosphates (e.g., tri-n-butyl phosphate (TBP)) in any combination. A particularly preferred trialkyl phosphate in certain embodiments comprises tri-n-butyl phosphate, which is a plasticizer. Moreover, in a preferred embodiment, each alkyl group of the di- or trialkyl phosphate has from one to ten or more carbon atoms, more preferably two to eight carbon atoms. The present invention also contemplates that each alkyl group of the di- or trialkyl phosphate may or may not be identical to one another.

In certain embodiments, mixtures of different dialkyl and trialkyl phosphates can be employed. In those embodiments comprising one or more alcohols as solvents, such solvents include, but are not limited to, methanol, ethanol, propanol and octanol. In a particularly preferred embodiment, the alcohol is ethanol. In those embodiments of the present invention intended for consumption by, or contact to, a host, the oil phase, and any additional compounds provided in the oil phase, may further be sterile and pyrogen free.

C. Surfactants and Detergents

In some embodiments, a nanoemulsion further comprises one or more surfactants or detergents (e.g., from about 3 to 15%, and preferably about 10%, although higher and lower amounts are contemplated). While the present invention is not limited to any particular mechanism, and an understanding of the mechanism is not required to practice the present invention, it is contemplated that surfactants help to stabilize the compositions (e.g., used to generate an immune response in a subject (e.g., used as a vaccine). Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers. Thus, in certain preferred embodiments, a nanoemulsion comprises one or more non-ionic surfactants such as polysorbate surfactants (e.g., polyoxyethylene ethers), polysorbate detergents, pheoxypolyethoxyethanols, and the like. Examples of polysorbate detergents useful in the present invention include, but are not limited to, TWEEN 20, TWEEN 40, TWEEN 60, TWEEN 80, etc.

TWEEN 60 (polyoxyethylenesorbitan monostearate), together with TWEEN 20, TWEEN 40 and TWEEN 80, comprise polysorbates that are used as emulsifiers in a number of pharmaceutical compositions. In some embodiments of the present invention, these compounds are also used as co-components with adjuvants. TWEEN surfactants also appear to have virucidal effects on lipid-enveloped viruses (See e.g., Eriksson et al., Blood Coagulation and Fibtinolysis 5 (Suppl. 3):S37-S44 (1994)).

Examples of pheoxypolyethoxyethanols, and polymers thereof, useful in the present invention include, but are not limited to, TRITON (e.g., X-100, X-301, X-165, X-102, X-200), and TYLOXAPOL. TRITON X-100 is a strong non-ionic detergent and dispersing agent widely used to extract lipids and proteins from biological structures. It also has virucidal effect against broad spectrum of enveloped viruses (See e.g., Maha and Igarashi, Southeast Asian J. Trop. Med. Pub. Health 28:718 (1997); and Portocala et al., Virologie 27:261 (1976)). Due to this anti-viral activity, it is employed to inactivate viral pathogens in fresh frozen human plasma (See e.g., Horowitz et al., Blood 79:826 (1992)).

In particularly preferred embodiments, the surfactants TRITON X-100 (t-octylphenoxypolyethoxyethanol), and/or TYLOXAPOL are employed. Some other embodiments, employ spermicides (e.g., Nonoxynol-9). Additional surfactants and detergents useful in the compositions of the present invention may be ascertained from reference works (See e.g., McCutheon's Volume 1: Emulsions and Detergents—North American Edition, 2000).

The surfactant in a nanoemulsion of the invention can be any pharmaceutically acceptable ionic surfactant, pharmaceutically acceptable nonionic surfactant, pharmaceutically acceptable cationic surfactant, pharmaceutically acceptable anionic surfactant, and/or pharmaceutically acceptable zwitterionic surfactant. Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), herein incorporated by reference in its entirety. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, and/or a pharmaceutically acceptable zwitterionic polymeric surfactant.

In some embodiments, a nonionic surfactant utilized in a nanoemulsion of the invention is a poloxamer. Poloxamer are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, comprises a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

D. Cationic Halogen Containing Compounds

In some embodiments, nanoemulsions (e.g., used in an immunogenic composition of the present invention) further comprise a cationic halogen containing compound (e.g., from about 0.5 to 1.0 wt. % or more, based on the total weight of the emulsion, although higher and lower amounts are contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected, for example, from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with a particular cationic containing compound.

E. Germination Enhancers

In other embodiments of the present invention, nanoemulsion compositions further comprise one or more germination enhancing compounds (e.g., from about 1 mM to 15 mM, and more preferably from about 5 mM to 10 mM, although higher and lower amounts are contemplated). In preferred embodiments, the germination enhancing compound is provided in the aqueous phase prior to formation of the emulsion. The present invention contemplates that when germination enhancers are added to the disclosed compositions the sporicidal properties of the compositions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the compositions preferentially occurs when the spores initiate germination.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104, herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the compositions of the present invention. A candidate germination enhancer should meet two criteria for inclusion in the compositions of the present invention: it should be capable of being associated with a nanoemulsion and it should increase the rate of germination of a target spore when incorporated in the emulsions of the present invention.

F. Interaction Enhancers

In still other embodiments, a nanoemulsion may comprise one or more compounds capable of increasing the interaction of the nanoemulsion (i.e., "interaction enhancer") with a target pathogen (e.g., with a bacterial membrane or viral envelope). In some embodiments, the interaction enhancer is premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis (oxyethylenenitrilo) tetraacetic acid (EGTA) in a buffer (e.g., tris buffer)). It is understood that chelating agents are merely exemplary interaction enhancing compounds. Indeed, other agents that increase the interaction of a nanoemulsion with a pathogen are contemplated. In particularly preferred embodiments, the interaction enhancer is at a concentration of about 50 to about 250 µM, although higher and lower amounts are contemplated. One skilled in the art will be able to determine whether a particular agent has the desired function of acting as an interaction enhancer by applying such an agent in combination with a nanoemulsion composition of the present invention to a target pathogen and comparing the inactivation of the target when contacted by the admixture with inactivation of like targets by the composition of the present invention without the agent. For example, an agent that increases the interaction and thereby neutralizes (e.g., decreases or inhibits the growth of the pathogen) in comparison to that parameter in its absence is considered an interaction enhancer.

G. Other Components

In some embodiments, a nanoemulsion comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion are described below. Additionally, a number of specific, although exemplary, formulation recipes are also set forth below.

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, and U.S. Patent Application Nos. 20070036831, 20060251684, and 20050208083, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined by a sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1. These particular formulations may be found in U.S. Pat. No. 5,700,679 (NN); U.S. Pat. Nos. 5,618,840; 5,549,901 ($W_{80}8P$); and U.S. Pat. No. 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1

| | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |

TABLE 1-continued

| | Oil Phase Formula | Water to Oil Phase Ratio (Vol/Vol) |
|---|---|---|
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri (N-butyl) phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOXAPOL, about 8 vol. % of ethanol, about 1 vol. % of cetylpyridinium chloride (CPC), about 60 to 70 vol. % of oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of $DiH_2O$ (designated herein as $W_{80}5EC$).

In some embodiments, the present invention provides a nanoemulsion comprising from about 5 vol. % of Poloxamer-407, from about 8 vol. % of ethanol, from about 1 vol. % of CPC, about 64 vol. % of oil (e.g., soybean oil), and about 22 vol. % of $DiH_2O$ (designated herein as $P_{407}5EC$). Although an understanding of the mechanism is not necessary to practice the present invention, and the present invention is not limited to any particular mechanism, in some embodiments, a nanoemulsion comprising Poloxamer-407 does not elicit and/or augment immune responses (e.g., in the lung) in a subject. In some embodiments, various dilutions of a nanoemulsion provided herein (e.g., $P_{407}5EC$) can be utilized to treat (e.g., kill and/or inhibit growth of) bacteria (See, e.g., FIG. 17). In some embodiments, undiluted nanoemulsion is utilized. In some embodiments, $P_{407}5EC$ is diluted (e.g., in serial, two fold dilutions) to obtain a desired concentration of one of the constituents of the nanoemulsion (e.g., CPC (See, e.g., FIG. 17)).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of $DiH_2O$ (designated herein as $W_{20}5EC$).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., $DiH_2O$ or PBS). For example, the present invention contemplates formulations comprising about 2 vol. % of TRITON X-100, about 8 vol. % of ethanol, about 64 vol. % of soybean oil, and about 26 vol. % of $DiH_2O$ (designated herein as X2E). In other similar embodiments, a nanoemulsion comprises about 3 vol. % of TRITON X-100, about 8 vol. % of ethanol, about 64 vol. % of soybean oil, and about 25 vol. % of $DiH_2O$ (designated herein as X3E). In still further embodiments, the formulations comprise about 4 vol. % Triton of X-100, about 8 vol. % of ethanol, about 64 vol. % of soybean oil, and about 24 vol. % of $DiH_2O$ (designated herein as X4E). In yet other embodiments, a nanoemulsion comprises about 5 vol. % of TRITON X-100, about 8 vol. % of ethanol, about 64 vol. % of soybean oil, and about 23 vol. % of $DiH_2O$ (designated herein as X5E). In some embodiments, a nanoemulsion comprises about 6 vol. % of TRITON X-100, about 8 vol. % of ethanol, about 64 vol. % of soybean oil, and about 22 vol. % of $DiH_2O$ (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of $DiH_2O$ (designated herein as X8E). In still further embodiments, a nanoemulsion comprises about 8 vol. % of TRITON X-100, about 8 vol. % of ethanol, about 64 vol. % of olive oil, and about 20 vol. % of $DiH_2O$ (designated herein as X8E O). In yet another embodiment, a nanoemulsion comprises 8 vol. % of TRITON X-100, about 8 vol. % ethanol, about 1 vol. % CPC, about 64 vol. % of soybean oil, and about 19 vol. % of $DiH_2O$ (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., $DiH_2O$ or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of $DiH_2O$ (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of $DiH_2O$ (designated herein as X2Y2PC STS1). In another similar embodiment, a nanoemulsion comprises about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of $DiH_2O$ (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of $DiH_2O$ (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of $DiH_2O$ (designated herein as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., $DiH_2O$ or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of $DiH_2O$ (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, a nanoemulsion comprises about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC 10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsions that find use (e.g., to inactivate and/or neutralize a pathogen, and for generating an immune response in a subject (e.g., for use as a vaccine)) in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, a nanoemuslion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2%

W$_{20}$5EC, 2% Methocel K, and 96% diH$_2$O (designated herein as 2% W$_{20}$5EC Methocel K); 2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% Triton X-100, 54% Soybean Oil, and 20% diH$_2$O (designated herein as X8PC$_{10}$); 5% Cetylpyridinium Chloride, 8% Triton X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1EC$_{0.2}$); 1% Cetylpyridinium Chloride, 5% TWEEN 20, 8% Glycerol, 64% Mobil 1, and 22% diH$_2$O (designated herein as W$_{20}$5GC Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1× PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while possessing potency against a broad range of microorganisms including bacteria, fungi, viruses, and spores. While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprise a mixture of oils, detergents, solvents, and cationic halogen-containing compounds in addition to several ions that enhance their biocidal activities. These SLPs are characterized as stable, non-irritant, and non-toxic compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 µM-20 mM)); and amino acids (e.g., L-alanine (50 µM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5 (2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl) benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl)ammonium chloride (C12-18);

Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysilypropyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as, for example, 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

The present invention is not limited by the type of subject administered a composition of the present invention. Each of the subjects (e.g., susceptible to respiratory infection) described above may be administered a composition of the present invention. In addition, the compositions and methods of the present invention are useful in the treatment of other respiratory diseases and disorders, such as acute bronchitis, bronchiectasis, pneumonia (including ventilator-associated pneumonia, nosocomial pneumonia, viral pneumonia, bacterial pneumonia, mycobacterial pneumonia, fungal pneumonia, eosinophilic pneumonia, and *Pneumocystis carinii* pneumonia), tuberculosis, cystic fibrosis (CF), emphysema radiation pneumonitis, and respiratory infection associated with inflammation caused by smoking, pulmonary edema, pneumoconiosis, sarcoidiosis, silicosis, asbestosis, berylliosis, coal worker's pneumonoconiosis (CWP), byssinosis, interstitial lung diseases (ILD) such as idiopathic pulmonary fibrosis, ILD associated with collagen vascular disorders, systemic lupus erythematosus, rheumatoid arthritis, ankylosing spondylitis, systemic sclerosis, and pulmonary inflammation that is a result of or is secondary to another disorder such as influenza.

The present invention is not limited by the particular formulation of a composition comprising a nanoemulsion of the present invention. Indeed, a composition comprising a nanoemulsion of the present invention may comprise one or more different agents in addition to the nanoemulsion. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion of the present invention comprises an agent and/or co-factor that enhance the ability of the nanoemulsion to kill a microbe (e.g., located in the respiratory tract). In some preferred embodiments, the presence of one or more co-factors or agents reduces the amount of nanoemulsion required for killing and/or attenuation of growth of a microbe. The present invention is not limited by the type of co-factor or agent used in a therapeutic agent of the present invention.

In some embodiments, a co-factor or agent used in a nanoemulsion composition is a bioactive agent. For example, in some embodiments, the bioactive agent may be a bioactive agent useful in a cell (e.g., a cell expressing a CFTR). Bioactive agents, as used herein, include diagnostic agents such as radioactive labels and fluorescent labels. Bioactive agents also include molecules affecting the metabolism of a cell (e.g., a cell expressing a CFTR), including peptides, nucleic acids, and other natural and synthetic drug molecules. Bioactive agents include, but are not limited to, adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LHRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; vulnerary; wound healing agent; xanthine oxidase inhibitor.

Molecules useful as antimicrobials can be delivered by the methods and compositions of the invention, such that the respiratory infection is reduced or eliminated. Antibiotics that may find use in co-administration with a composition comprising a nanoemulsion of the present invention include, but are not limited to, agents or drugs that are bactericidal and/or bacteriostatic (e.g., inhibiting replication of bacteria or inhibiting synthesis of bacterial components required for survival of the infecting organism), including, but not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveninomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, Pep5, RP 59500, and TD-6424.

In some embodiments, a composition comprising a nanoemulsion of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a nanoemulsion) enhances killing and/or attenuation of growth of a microbe (e.g., exposed to a composition of the present invention) due to an increase in duration and/or amount of exposure to the nanoemulsion that a subject and/or microbe experiences when a mucoadhesive is used compared to the duration and/or amount of exposure to the nanoemulsion in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, pulmonary, subcutaneous, intramuscular, intraperitoneal, intravenous, or administration via other routes may be found in Remington's Pharmaceutical Sciences, Mack Publishing Company, Easton, Pa.

A composition comprising a nanoemulsion of the present invention can be used therapeutically (e.g., to kill and/or attenuate growth of an existing infection) or as a prophylactic (e.g., to prevent microbial growth and/or colonization (e.g., to prevent signs or symptoms of disease)). A composition comprising a nanoemulsion of the present invention can be administered to a subject via a number of different delivery routes and methods.

For example, the compositions of the present invention can be administered to a subject (e.g., mucosally or by pulmonary route) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal or pulmonary surface); being placed on or impregnated onto a nasal and/or pulmonary applicator and applied; being applied by a controlled-release mechanism; applied using a nebulizer, aerosolized, being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal and pulmonary techniques), as well as European Publication No. 517,565 and Illum et al., J. Controlled Rel., 1994, 29:133-141 (e.g., for techniques of intranasal administration), each of which is hereby incorporated by reference in its entirety). The present invention is not limited by the route of administration.

Methods of intranasal and pulmonary administration are well known in the art, including the administration of a droplet or spray form of the nanoemulsion into the nasopharynx of a sujbect to be treated. In some embodiments, a nebulized or aerosolized composition comprising a nanoemulsion is provided. Enteric formulations such as gastro resistant capsules for oral administration, suppositories for rectal or vaginal administration may also form part of this invention. Compositions of the present invention may also be administered via the oral route. Under these circumstances, a composition comprising a nanoemulsion may comprise a pharmaceutically acceptable excipient and/or include alkaline buffers, or enteric capsules. Formulations for nasal delivery may include those with dextran or cyclodextran and saponin as an adjuvant.

In preferred embodiments, a nanoemulsion of the present invention is administered via a pulmonary delivery route and/or means. In some embodiments, an aqueous solution containing the nanoemulsion is gently and thoroughly mixed to form a solution. The solution is sterile filtered (e.g., through a 0.2 micron filter) into a sterile, enclosed vessel. Under sterile conditions, the solution is passed through an appropriately small orifice to make droplets (e.g., between 0.1 and 10 microns).

The particles may be administered using any of a number of different applicators. Suitable methods for manufacture and administration are described in the following U.S. Pat. Nos. 6,592,904; 6,518,239; 6,423,344; 6,294,204; 6,051,256 and 5,997,848 to INHALE (now NEKTAR); and U.S. Pat. No. 5,985,309; RE37,053; U.S. Pat. Nos. 6,436,443; 6,447,753; 6,503,480; and 6,635,283, to Edwards, et al. (MIT, AIR), each of which is hereby incorporated Thus, in some embodiments, compositions of the present invention are administered by pulmonary delivery. For example, a composition of the present invention can be delivered to the lungs of a subject (e.g., a human) via inhalation (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140: 3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)). In some embodiments, a composition comprising a nanoemulsion is administered to a subject by more than one route or means (e.g., administered via pulmonary route as well as a mucosal route).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the ULTRAVENT nebulizer (Mallinckrodt Inc., St. Louis, Mo.); the ACORN II nebulizer (Marquest Medical Products, Englewood, Colo.); the VENTOLIN metered dose inhaler (Glaxo Inc., Research Triangle Park, N.C.); and the SPINHALER powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a nanoemulsion of the present invention may be used to protect and/or treat a subject susceptible to, or suffering from, a disease by means of administering compositions comprising a nanoemulsion by mucosal, intramuscular, intraperitoneal, intradermal, transdermal, pulmonary, intravenous, subcutaneous or other route of administration described herein. Methods of systemic administration of the nanoemulsion and/or agent co-administered with the nanoemulsion may include conventional syringes and needles, or devices designed for ballistic delivery (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with the nanoemulsion composition of the present invention.

As described above, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., subjects with CF or asthma, subjects in the armed forces, government employees, frequent travelers, persons attending or working in a school or daycare, health care workers, an elderly person, an immunocompromised person, and emergency service employees (e.g., police, fire, EMT employees)). In some embodiments, any one or all members of the general public can be administered a composition of the present invention (e.g., to prevent the occurrence or spread of disease). For example, in some embodiments, compositions and methods of the present invention are utilized to treat a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition comprising a nanoemulsion of the present invention can be administered (e.g., to a subject (e.g., via pulmonary and/or mucosal route) or to microbes (e.g., bacteria (e.g., opportunistic and/or pathogenic bacteria (e.g., residing on or within the respiratory system of a subject)))) as a therapeutic or as a prophylactic to prevent microbial infection. Thus, in some embodiments, the present invention provides a method of altering microbial (e.g., bacterial (e.g., opportunistic and/or pathogenic bacterial) growth comprising administering a composition comprising a nanoemulsion to the microbes (e.g., bacteria (e.g., opportunistic and/or pathogenic bacteria). In some embodiments, administration of a composition comprising a nanoemulsion to the microbes (e.g., bacteria (e.g., opportunistic and/or pathogenic bacteria) kills the microbes. In some embodiments, administration of a composition comprising nanoemulsion to the microbes (e.g., bacteria (e.g., opportunistic and/or pathogenic bacteria) inhibits growth of the microbes. It is contemplated that a composition comprising a nanoemulsion can be administered to microbes (e.g., bacteria (e.g., opportunistic and/or pathogenic bacteria (e.g., residing within the respiratory tract))) via a number of delivery routes and/or mechanisms.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the nanoemulsion. In some embodiments, nanoemulsion compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a nanoemulsion is co-administered with one or more antibiotics. For example, one or more antibiotics may be administered with, before and/or after administration of a composition comprising a nanoemulsion. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a nanoemulsion with one or more additional active and/or anti-infective agents. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, a second type of nanoemulsion, etc.) can be any of the well-known agents in the art, including, but not limited to, those that are currently in clinical use.

In some embodiments, a composition comprising a nanoemulsion is administered to a subject via more than one route. For example, a subject may benefit from receiving mucosal administration (e.g., nasal administration or other mucosal routes described herein) and, additionally, receiving one or more other routes of administration (e.g., pulmonary administration (e.g., via a nebulizer, inhaler, or other methods described herein.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a nanoemulsion of the present invention comprises a suitable amount of the nanoemulsion to kill and/or attenuate growth of microbes (e.g., pathogenic microbes (e.g., pathogenic bacteria, viruses, etc.)) in a subject when administered to the subject. The present invention is not limited by the amount of nanoemulsion used. In some preferred embodiments, the amount of nanoemulsion in a composition comprising a nanoemulsion is selected as that amount which kills and/or attenuates microbial growth without significant, adverse side effects. The amount will vary depending upon which specific nanoemulsion(s) is/are employed, and can vary from subject to subject, depending on a number of factors including, but not limited to, the species, age and general condition (e.g., health) of the subject, and the mode of administration. Procedures for determining the appropriate amount of nanoemulsion administered to a subject to kill and/or attenuate growth of a microbe (e.g., pathogenic microbe (e.g., pathogenic bacteria, viruses, etc.)) in a subject can be readily determined using known means by one of ordinary skill in the art.

In some embodiments, it is expected that each dose (e.g., of a composition comprising a nanoemulsion (e.g., administered to a subject to kill and/or attenuate microbial growth)) comprises 10-40% nanoemulsion, in some embodiments, 20% nanoemulsion, in some embodiments less than 20% (e.g., 15%, 10%, 8%, 5% or less nanoemulsion), and in some embodiments greater than 20% nanoemulsion (e.g., 25%, 30%, 35%, 40% or more nanoemulsion). An optimal amount for a particular administration (e.g., to kill and/or attenuate microbial growth) can be ascertained by one of skill in the art using standard studies involving observation of microbial growth and/or death and other responses in subjects.

In some embodiments, it is expected that each dose (e.g., of a composition comprising a nanoemulsion (e.g., administered to a subject to kill and/or attenuate microbial growth)) is from 0.001 to 40% or more (e.g., 0.001-10%, 0.5-5%, 1-3%, 2%, 6%, 10%, 15%, 20%, 30%, 40% or more) by weight nanoemulsion.

Similarly, the present invention is not limited by the duration of time a nanoemulsion is administered to a subject (e.g., to kill and/or attenuate microbial growth). In some embodiments, a nanoemulsion is administered one or more times (e.g. twice, three times, four times or more) daily. In some embodiments, a composition comprising a nanoemulsion is administered one or more times a day until an infection is eradicated or microbial growth and/or presence has been reduced to a desired level. In some embodiments, a composition comprising a nanoemulsion of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the nanoemulsion present in the concentrated composition. Concentrated compositions are contemplated to be useful in a setting in which large numbers of subjects may be administered a composition of the present invention (e.g., a hospital). In some embodiments, a composition comprising a nanoemulsion of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Dosage units may be proportionately increased or decreased based on several factors including, but not limited to, the weight, age, and health status of the subject. In addition, dosage units may be increased or decreased for subsequent administrations.

In some embodiments, a composition comprising a nanoemulsion is administered to a subject under conditions such that microbes (e.g., bacteria (e.g., opportunistic and/or pathogenic bacteria)) are killed. In some embodiments, a composition comprising a nanoemulsion is administered to a subject under conditions such that microbial (e.g., bacterial (e.g., opportunistic and/or pathogenic bacterial) growth is prohibited and/or attenuated. In some embodiments, greater than 90% (e.g., greater than 95%, 98%, 99%, all detectable) of microbes (e.g., bacteria (e.g., opportunistic and/or pathogenic bacteria) are killed. In some embodiments, there is greater than 2 log (e.g., greater than 3 log, 4 log, 5 log, or more) reduction in microbe (e.g., bacteria (e.g., opportunistic and/or pathogenic bacteria) presence. In some embodiments, reduction and/or killing is observed in one hour or less (e.g., 45 minutes, 30 minutes, 15 minutes, or less). In some embodiments, reduction and/or killing is observed in 6 hours or less (e.g., 5 hours, 4, hours, 3 hours, two hours or less than one hour). In some embodiments, reduction and/or killing is observed in two days or less following initial treatment (e.g., less than 24 hours, less than 20 hours, 18 hours or less). In some embodiments, the reduction and/or killing is observed in three days or less, four days or less, or five days or less.

A composition comprising a nanoemulsion of the present invention finds use where the nature of the infectious and/or disease causing agent (e.g., causing signs, symptoms or indications of respiratory infection) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of infections associated with an emergent infectious and/or disease causing agent yet to be identified (e.g., isolated and/or cultured from a diseased person but without genetic, biochemical or other characterization of the infectious and/or disease causing agent).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of pulmonary, mucosal and other routes of delivery. As is readily apparent, the compositions of the present invention are useful for preventing and/or treating a wide variety of diseases and infections caused by viruses, bacteria, parasites, and fungi. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest.

In some embodiments, the present invention provides a kit comprising a composition comprising a nanoemulsion. In some embodiments, the kit further provides a device for administering the composition. The present invention is not limited by the type of device included in the kit. In some embodiments, the device is configured for pulmonary application of the composition of the present invention (e.g., a nasal inhaler or nasal mister). In some embodiments, a kit comprises a composition comprising a nanoemulsion in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit components are located in a single container (e.g., vial or tube) with other components of the same kit being located in a separate container (e.g., vial or tube). In some embodiments, a kit comprises a buffer. In some embodiments, the kit further comprises instructions for use.

EXPERIMENTAL

The following examples are provided in order to demonstrate and further illustrate certain preferred embodiments and aspects of the present invention and are not to be construed as limiting the scope thereof.

EXAMPLE 1

In Vivo Toxicity Studies

A nanoemulsion composition of the present invention was tested to determine if pulmonary administration of the composition to a subject would elicit any histological changes and/or pathology.

A solution comprising 20% nanoemulsion ($W_{80}5EC$) and 0.1% EDTA was administered via a nebulizer. A custom murine nose only nebulization chamber with PARI LC nebulizer (Midlothian, Va.) and compressor was used. A 0.9% NaCl solution was used as a control. Using the nebulizer, mice were administered nebulized nanoemulsion+EDTA or NaCl solution for 10 minutes. Twenty-four hours after administration, mice were sacrificed and physical properties and histology assessed.

Upon examination, there was an absence of histological changes indicating the absence of toxicity upon administration of nebulized nanoemulsion. Physical findings were normal.

EXAMPLE 2

Killing Assays Utilizing Nanoemulsion Compositions and Bacteria Found in the Respiratory Tract It was determined whether a composition comprising nanoemulsion ($W_{80}5EC$) alone or in combination with EDTA and/or the presence of a hypertonic salt solution would be able to attenuate growth and/or kill bacteria found in the respiratory tract.

An overnight culture of *Burkholderia cepacia* or *Pseudomonas aeruginosa* was started in 6 ml of cation adjusted Mueller Hinton Broth (MHB) from a frozen bacterial stock at −80° C. The culture was incubated in a shaking incubator at 37° C. The following day, bacteria were brought to logarithmic growth phase by back diluting the overnight culture 1:4 with fresh MHB. Back diluted culture was incubated at 37° C. in the shaking incubator until the OD600 reached between 0.40 to 0.45. One ml of the culture was spun down at 3500 to 4000 rpm for 15 minutes. The bacterial pellet was resuspended in 1 ml of sterile 2×PBS, 12% or 14% saline. Appropriate dilutions were done with the same solutions to get desired numbers of bacteria in 50 µl (OD600 of 0.5 approximately =$10^9$ bacteria). Dilutions of the starting bacterial suspensions were plated onto Luria Bertani (LB) agar plates to estimate the starting bacterial counts. Double the concentrations of the desired final nanoemulsion and nanoemulsion with EDTA concentrations were made with sterile milliQ water. Fifty micro liters of the nanoemulsion was mixed with 50 µl of the bacteria and vortexed to mix the reaction. The mixture was incubated at 37° C. for desired time intervals. Following incubation, the reaction was diluted with 500 µl of 1×PBS and vortexed to mix the contents. The contents were centrifuged at 4000 rpm for 15 minutes to pellet the bacteria and separate the nanoemulsion. Supernatant containing the nanoemulsion was removed and the bacterial pellet resuspended in 1×PBS. Undiluted or dilutions of the resuspended bacterial pellet was plated onto LB agar plates for colony count. Log killing of the bacteria were calculated from ratio with the starting numbers.

Figure 2:
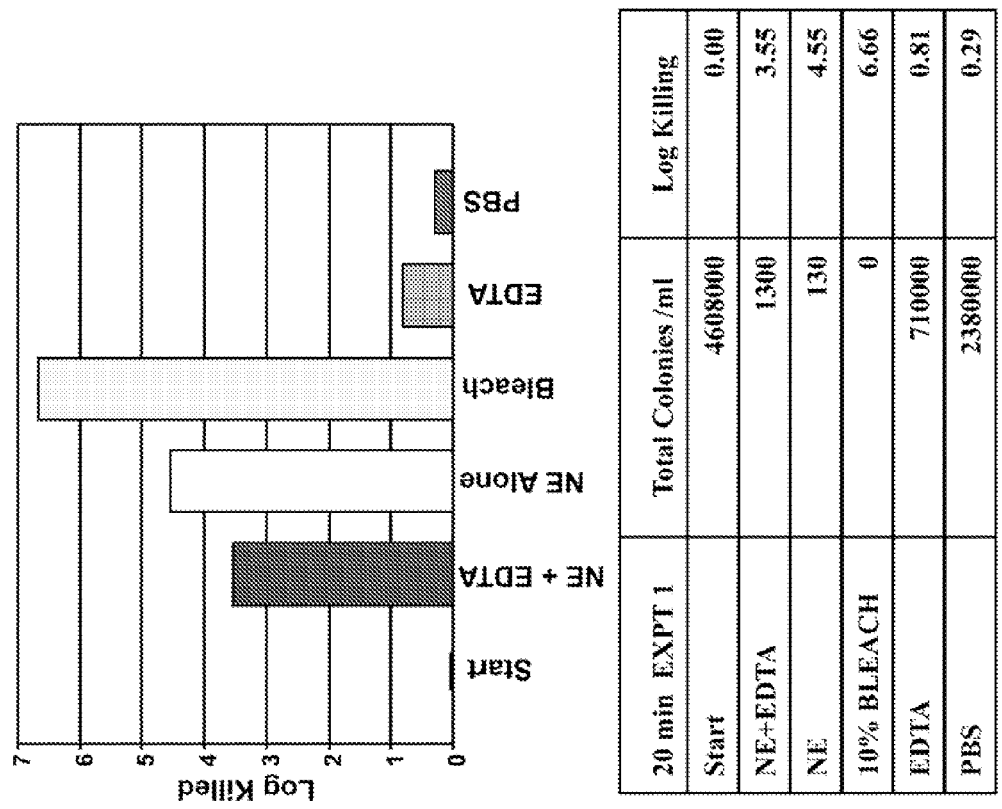
Figure 3:
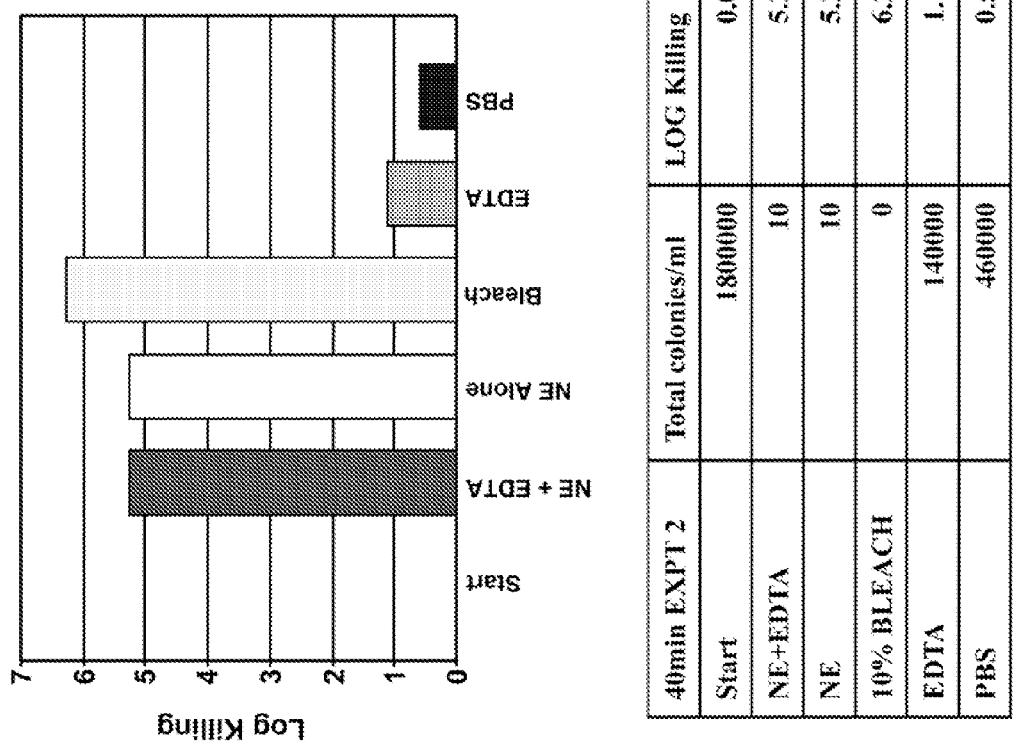
Figure 4A:
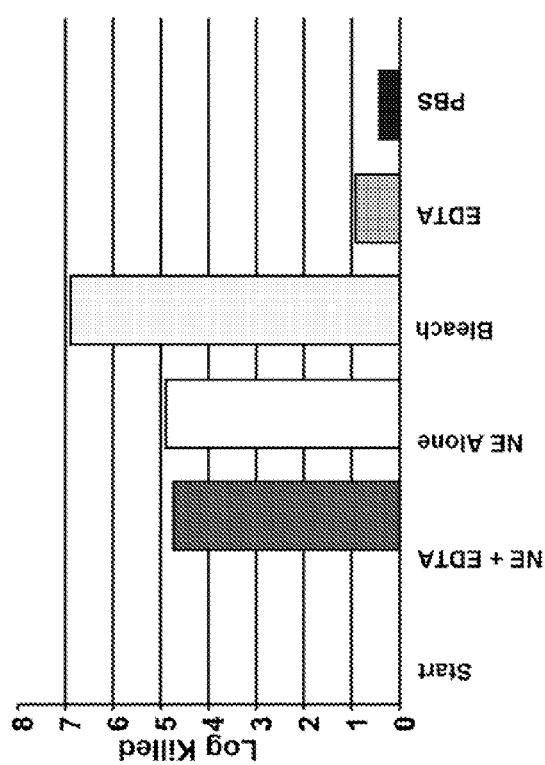
Figure 4B:
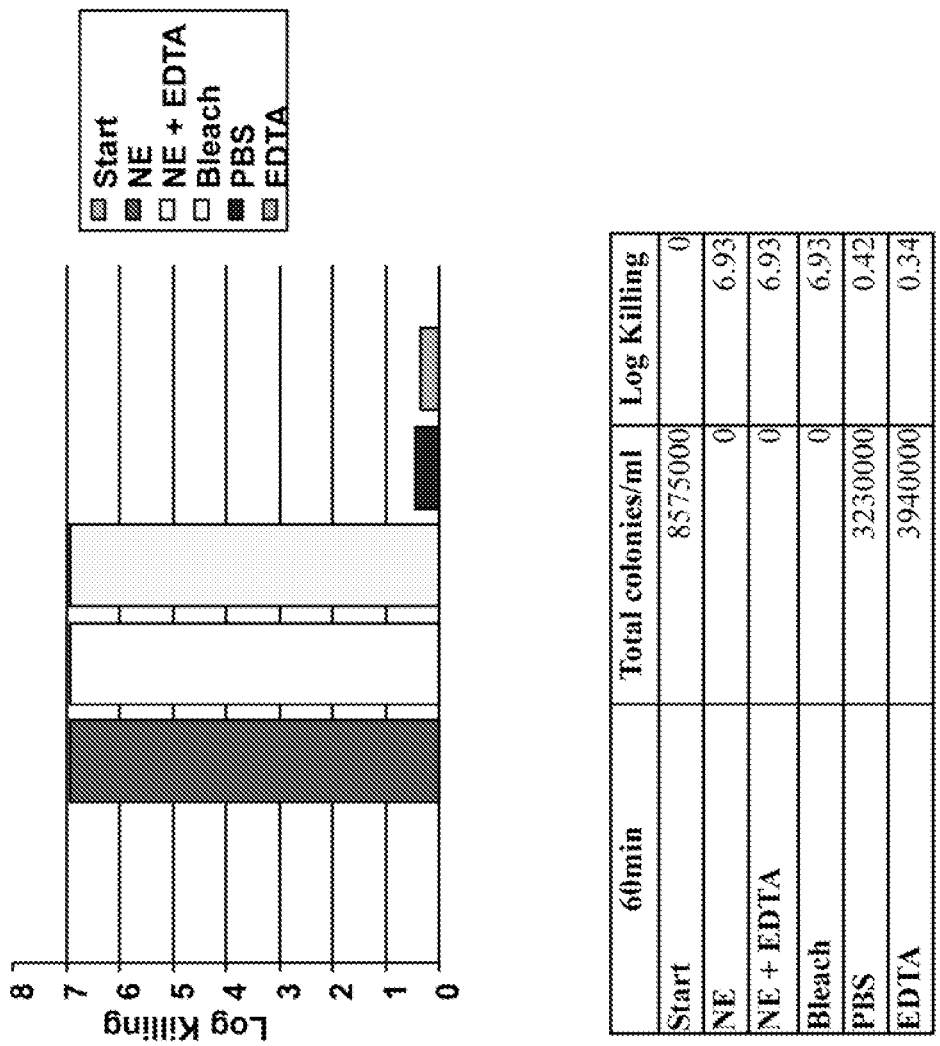
Figure 4C:
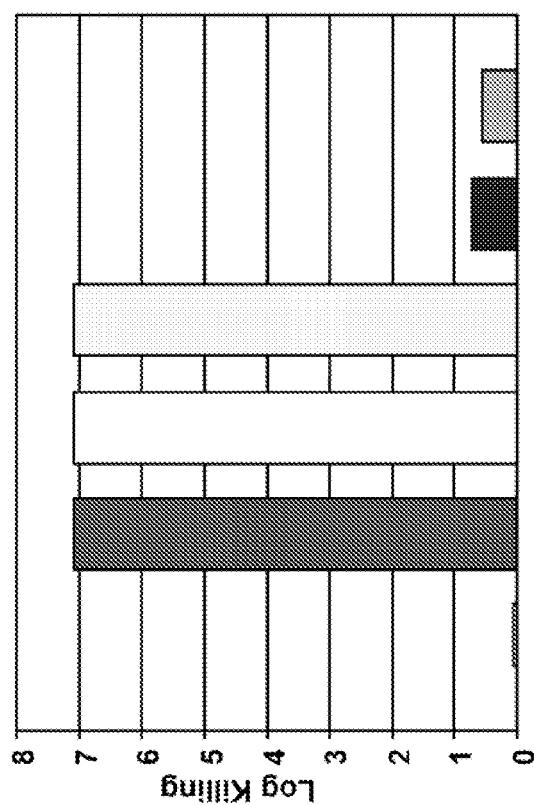
Figure 5:
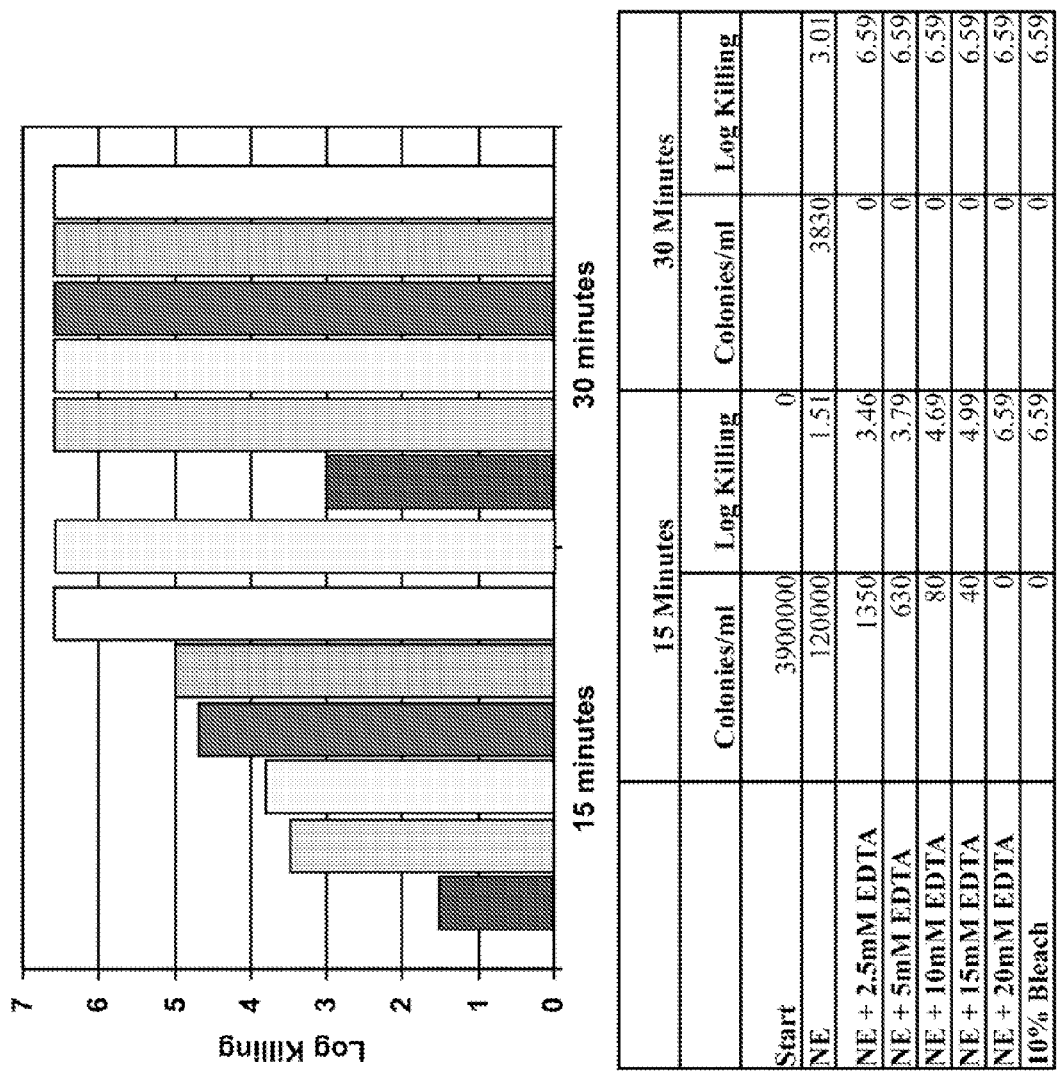
Figure 6:
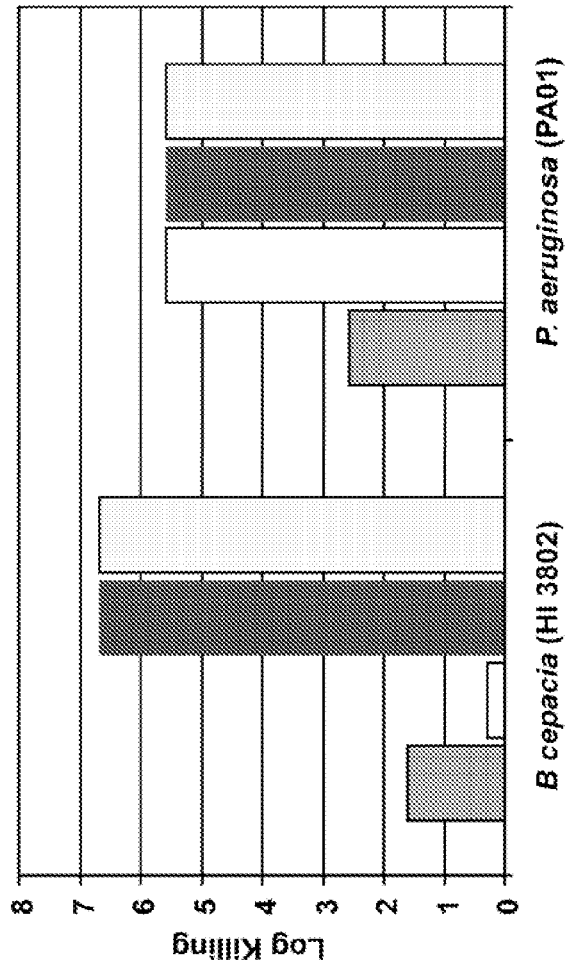
Figure 7:
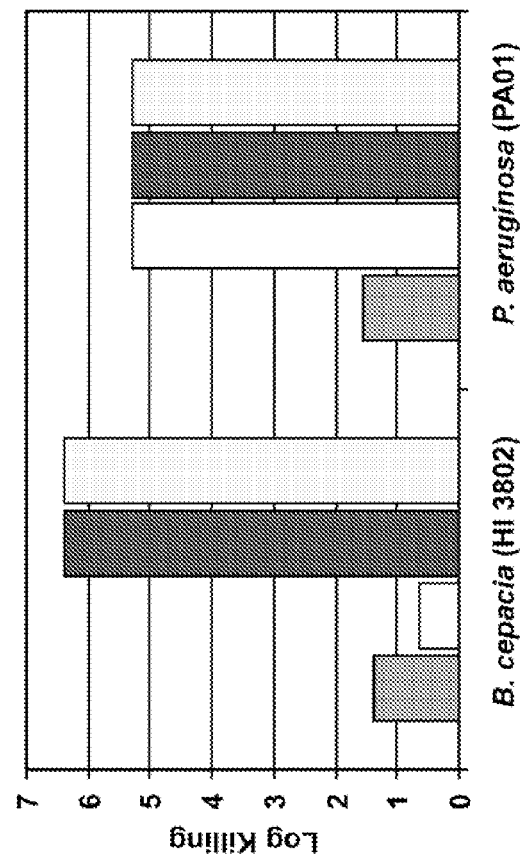

The following killing assays were performed:

Killing of *Burkholderia cepacia* in PBS by 20% Nanemulsion (NE) alone or with 20 mM EDTA in 10 minutes (See FIG. 1);

Killing of *B. cepacia* in PBS by 20% NE alone or with 20 mM EDTA within 20 minutes (See FIG. 2);

Killing of *B. cepacia* in PBS by 20% NE alone or with 20 mM EDTA within 40 minutes (See FIG. 3);

Killing of *B. cepacia* in PBS by 20% NE alone or with 20 mM EDTA within 40 or 60 minutes (See FIG. 4);

Killing of *B. cepacia* in hypertonic saline (6% NaCl) at 15 and 30 minutes by NE alone and NE with EDTA (See FIG. 5);

Killing of *B. cepacia* and *P. aeruginosa* in 7% NaCl within 15 min (See FIG. 6); and Killing of *B. cepacia* and *P. aeruginosa* (Mixed-culture) in 7% NaCl within 15 minutes (See FIG. 7).

Nanoemulsion alone or in combination with EDTA (e.g., 10-20 mM EDTA) was able to achieve complete killing of $10^6$ bacteria in PBS in 60 minutes. In the presence of hypertonic saline (e.g., 6-7% NaCl), the killing ability of the nanoemulsion was strikingly enhanced, achieving complete killing within 15 minutes while in the presence of 20 mM EDTA. Also, nanoemulsions comprising a lower concentration of EDTA were able to achieve complete killing of bacteria in 30 minutes in the presence of hypertonic saline. Thus, the present invention provides that a nanoemulsion composition comprising EDTA can be used to kill (e.g., completely) bacteria over a short time period (e.g., <60 minutes). Moreover, the present invention provides that nanoemulsion with hypertonic saline and EDTA can be used to kill bacteria over even shorter time periods (e.g., <30 minutes, <15 minutes) and that the concentration of EDTA and hypertonic saline solution alter the pace at which the nanoemulsion is able to eradicate the bacteria. The present invention also demonstrates that compositions of the present invention are able to eradicate a mixed population of bacteria.

EXAMPLE 3

Nanoemulsion Killing of Cystic Fibrosis (CF) Related Bacteria Including Multi-Drug Resistant Strains Materials and Methods.

Bacterial strains and culture conditions. One hundred fifty isolates were analyzed including 75 *Burkholderia* isolates and 75 isolates belonging to other CF-relevant species, including *Pseudomonas aeruginosa*, *Achromobacter xylosoxidans*, *Stenotrophomonas maltophilia*, *Acinetobacter* species, *Pandoraea* species (*P. apista*, *P. pnomenusa*, *P. pulmonicola*, *P. norimburgensis*, and *P. sputorum*), and *Ralstonia* species (*R. mannitolilytica* and *R. pickettii*). One hundred forty-five clinical isolates were obtained from the *Burkholderia cepacia* Research Laboratory and Repository (BcRLR, University of Michigan, Ann Arbor, Mich.). These were recovered from 142 individuals between September 1997 and October 2007 and were referred to the BcRLR from 62 CF treatment centers in the U.S. for analysis. The remaining five strains included environmental isolates *B. multivorans* ATCC 17616 (American Type Culture Collection, Manassas, Va.), *P. norimburgensis* LMG 18379$^T$ (BCCM/LMG Bacteria Collection, Laboratorium voor Micrbiologie Gent, Universiteit Gent, Ghent, Belgium) and *B. pyrrocinia* HI3642 (BcRLR collection), and the clinical type strains *B. cenocepacia* LMG 16656$^T$ (aka J2315) and *P. pulmonicola* LMG 18106$^T$. One hundred thirty four (91%) of the 147 clinical isolates were recovered from persons with CF; 114 (78%) of these were from sputum culture, with the remainder from throat swab (n=17), endotracheal suction/tracheal aspiration (n=5), blood (n=5), bronchial lavage (n=3), and one each from maxillary sinus, peritoneal cavity, and epiglottis. Forty nine (33%) of the 150 isolates were defined as multi-drug resistant (resistant to all drugs tested in two of three antibiotic classes: lactams including carbapenems, aminoglycosides, and quinolones; See, e.g., Taccetti et al., Eur J. Epidemiol. 1999 January; 15(1):85-8) based on susceptibility testing performed at the referring microbiology laboratory; 20 (41%) of these were panresistant. Seventy two (48%) of the remaining isolates were susceptible to at least one antibiotic, and susceptibility testing results were unavailable for 29 (19%) isolates. All isolates were identified to the species level at the BcRLR by polyphasic analyses using phenotypic and genotypic assays as described (See, e.g., Reik et al., J Clin Microbiol. 2005 June; 43(6):2926-8). The exception was *Acinetobacter*, which was identified only to the genus level due to lack of definitive species-specific assays. All isolates were also subjected to repetitive extragenic element-PCR (rep-PCR) typing using the BOX AIR primer as previously described (See, e.g., Coenye et al., J Clin Microbiol. 2002 September; 40(9): 3300-7) to ensure that all 150 isolates included in the test panel were genotypically distinct. Bacteria were stored at −80° C. in skim milk or Lauria-Bertani (LB) broth with 15% glycerol and recovered from frozen stock overnight at 37° C. on Mueller-Hinton (MH) agar.

Nanoemulsion. Nanoemulsion $P_{407}5EC$, described herein, was manufactured by NANOBIO Corp. (Ann Arbor, Mich.). $P_{407}5EC$ droplets had a mean particle diameter of 400 nm. Surfactants and food substances utilized in the manufacture of $P_{407}5EC$ were 'Generally Recognized as Safe' (GRAS) by the FDA, and manufactured in accordance with Good Manufacturing Practices (GMP). The concentration of CPC was used as a surrogate for the amount of $P_{407}5EC$ used experimentally. $P_{407}5EC$ was stable for no less than 12 months at 40° C.

Susceptibility testing. Because $P_{407}5EC$ is opaque, the MICs of this compound for test bacteria were determined by using a modification of the Clinical and Laboratory Standards Institute (CLSI)-approved microtiter serial dilution method (See, e.g., Clinical and Laboratory Standards Institute. 2006. Approved standard M7-A7, seventh edition. Clinical and Laboratory Standards Institute, Wayne, Pa.). $P_{407}5EC$ was diluted to a concentration of 2 mg/ml (of CPC) in MH broth supplemented with 7% NaCl and 20 mM EDTA. Serial two-fold dilutions of this preparation were made in unsupplemented MH broth and aliquoted into 96-well flat bottom microtiter plates (100 μl/well). Bacteria from overnight growth on MH agar were suspended in MH broth to a 0.5 McFarland turbidity standard (absorbance of 0.08-0.13 at 625 nm), further diluted 1:100 in MH broth, and added (5 μl/well) to the $P_{407}5EC$ serial dilution wells. Appropriate controls, including wells with bacteria but no $P_{407}5EC$ and wells with $P_{407}5EC$ dilutions but no bacteria, were included on each plate. Microtiter plates were shaken briefly, and 1 μl was removed from wells containing bacteria but no $P_{407}5EC$, diluted in 1 ml of MH broth, plated on MH agar (100 μl), and incubated for 24-48 h at 37° C. to determine bacterial concentrations of initial inoculums. Microtiter plates were then incubated at 37° C. without shaking. To determine MBCs, 10 μl were removed from each well after overnight growth, spotted on MH agar, and incubated at 37° C. Colonies were enumerated 24 h later, and MBCs were recorded as the $P_{407}5EC$ concentration with a 3 log decrease in CFU/ml compared to the initial inoculum. To determine MICs, 10 μl of resazurin (R&D SYSTEMS, Minneapolis, Minn.) were added to each well and microtiter plates were shaken briefly, covered with foil, and incubated at 37° C. without shaking. Wells were visually inspected the next day, and the MIC was recorded as the lowest concentration of $P_{407}5EC$ remaining a blue color. MIC results were further quantified by recording fluorescence on a spectrofluorometer at 560 nm excitation/590 nm emission.

Biofilm growth and susceptibility testing. To identify biofilm-forming isolates, bacteria were grown overnight in tryptic soy broth, adjusted to a 0.5 McFarland turbidity standard, and further diluted 1:10 in MH broth, and 100 μl were seeded in triplicate in internal wells of 96-well flat bottom microtiter plates. Negative control wells without bacteria were included. To minimize evaporation, the remaining wells were filled with MH broth, and the plate was wrapped with plastic wrap before incubating for 48 h at 37° C. without shaking. Wells were gently washed twice with phosphate buffered saline (PBS; pH 7.4), dried for 2 h at 37° C., and then stained with 1% crystal violet in water for 15 min. Stained wells were washed 3 times with PBS, and crystal violet was solubilized by the addition of absolute methanol. After incubation for 5 min at room temperature, the solubilized crystal violet was transferred to a new microtiter plate and scanned at 590 nm in a spectrophotometer. A biofilm-forming isolate was defined as one where the average absorbance of the 3 wells was greater than the average absorbance of the negative control wells plus 3 standard deviations (See, e.g., Stepanovic et al., J Microbiol Methods. 2000 April; 40(2):175-9).

For biofilm susceptibility testing, isolates shown to produce biofilm by crystal violet testing were grown in triplicate for 48 h as described above. Wells were gently washed twice with PBS before addition of $P_{407}5EC$, serially diluted as described for planktonic MIC testing. After overnight incubation at 37° C., wells were again washed twice with PBS, and 100 μl of 10% resazurin in MH broth was added to wells. Plates were wrapped in plastic, covered with foil, and again incubated overnight at 37° C. without shaking. Plates were visually inspected the next day, and the minimum biofilm inhibitory concentration (MBIC) was recorded as the lowest concentration of $P_{407}5EC$ in which the wells were a blue color. To calculate minimum biofilm eradication concentrations (MBECs), biofilm was resuspended in the same wells used for MBIC testing by shaking the microtiter plate and then scraping the sides of the wells with a pipet tip. Ten μL were removed from each well, spotted on MH agar plates and incubated at 37° C. After overnight growth, MBECs were recorded as the lowest $P_{407}5EC$ concentration resulting in no growth (See, e.g., Tomlin et al., Can J. Microbiol. 2001 October; 47(10):949-54). To confirm initial inoculum concentrations and to quantify viable bacteria in biofilm grown cultures, colonies were enumerated from 10-fold serial dilutions of the 0.5 McFarland inoculating culture and from the untreated positive control wells with resuspended biofilm for MBEC calculations.

Sputum preparation. Expectorated sputum, collected from CF patients during the course of routine care, was obtained from the University of Michigan Health System clinical microbiology laboratory and stored at −80° C. Equal volumes of sputum from 15 individuals were pooled, mechanically sheared using a TISSUE MISER homogenizer (FISHER SCIENTIFIC, Pittsburg, Pa.) at room temperature for 5 min at maximum speed, and then incubated in an 80° C. water bath for 20 min. Processed sputum was divided into 10 ml aliquots, and 100 μl from each aliquot was plated on MH agar and incubated for 48 h at 37° C. to confirm sterility. Aliquots were stored at −80° C.

Results.

Figure 8:
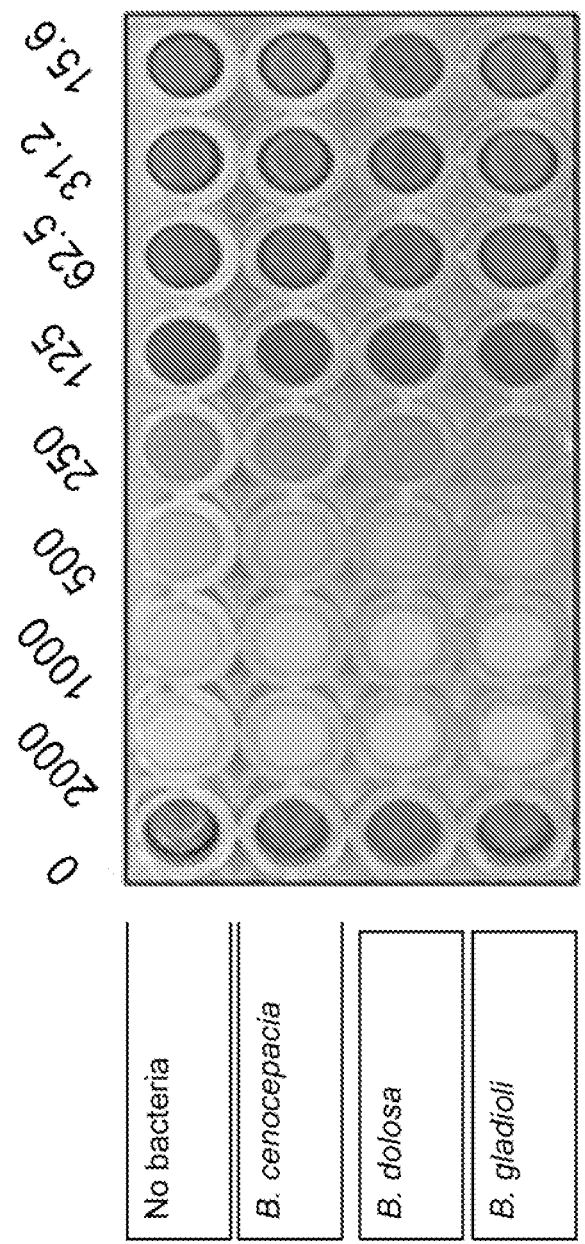
Figure 9:
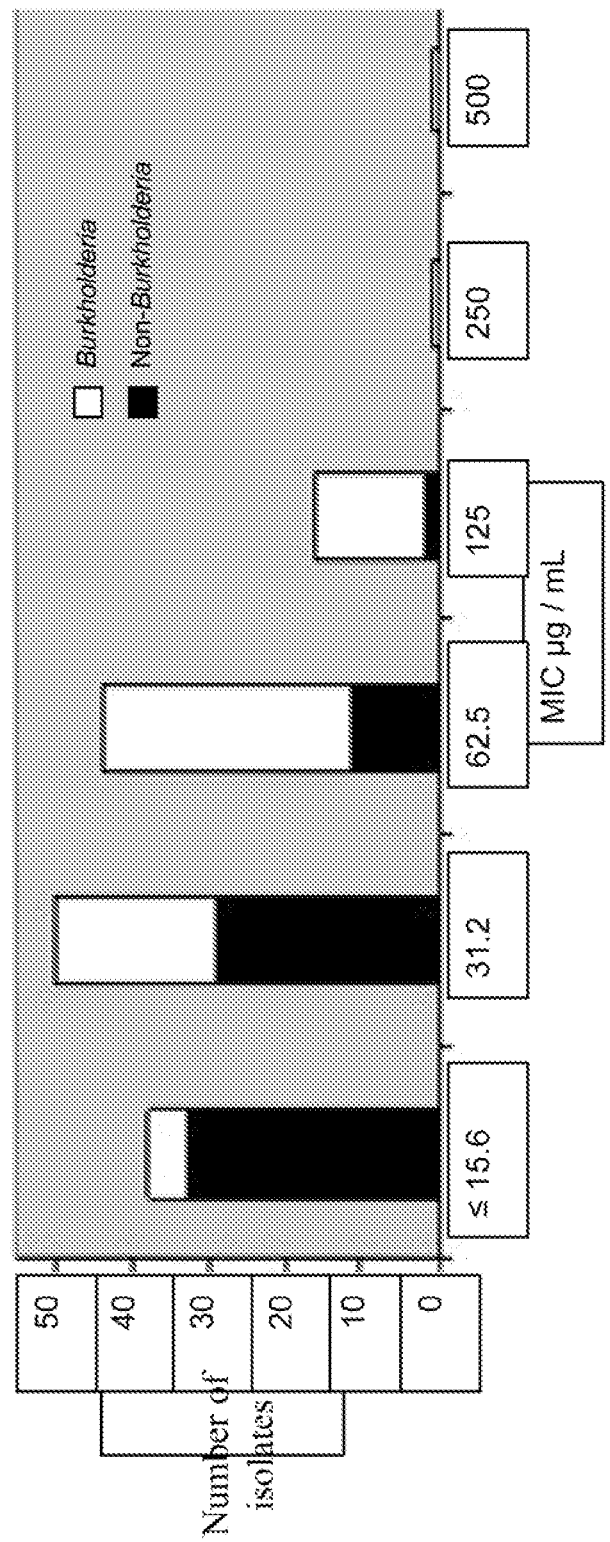

Susceptibility of planktonic bacteria. Due to the opaque white color of $P_{407}5EC$, the standard CLSI-approved microtiter serial dilution method was modified to include the addition of resazurin as an indicator of bacterial viability. $P_{407}5EC$ was tested in a concentration range of 15.6-2000 μg/ml. MICs were defined as the lowest concentration of $P_{407}5EC$ that did not produce a color change from blue to pink (See FIG. 8). Comparison of this visual inflection point with fluorometric analysis showed that 63% of MIC wells had ≤1% of the metabolic activity of untreated control wells; 91% had ≤5% metabolic activity, and 96% had ≤10% metabolic activity compared to control wells. The MIC results are shown in FIG. 11. All strains were inhibited by the concentrations of $P_{407}5EC$ tested. The $MIC_{50}$ for the entire panel of 150 strains was 31.2 μg/ml; the $MIC_{90}$ was 125 μg/ml. Thirty eight strains (25%) were inhibited by the lowest concentration of $P_{407}5EC$ tested (15.6 μg/ml), and only a single strain each required a concentration of 250 μg/ml and 500 μg/ml for inhibition. $P_{407}5EC$ was slightly more active against non-*Burkholderia* strains ($MIC_{50}$ 31.2 μg/ml; MICgo 62.5 μg/ml) than *Burkholderia* strains ($MIC_{50}$ 62.5 μg/ml; $MIC_{90}$ 125 μg/ml) (See FIG. 9). Activity was comparable across the 10 *Burkholderia* species tested. No difference was found in the activity of $P_{407}5EC$ against multi-drug resistant *Burkholderia* strains compared to strains susceptible to one or more antibiotics.

To evaluate the bactericidal activity of $P_{407}5EC$ against planktonic bacteria, MBCs were determined on a subset of 34 strains including 22 *Burkholderia* and 12 non-*Burkholderia*. All MBCs were within 1 dilution of the respective MICs for this subset of strains except for a single *B. cenocepacia* strain that had a MIC of 250 μg/ml and an MBC of 2000 μg/ml. A time-kill study of *B. multivorans* ATCC 17616 showed time- and concentration-dependent killing, with a 99% decrease in bacterial viability within 90 min at a $P_{407}5EC$ concentration two times greater than the MIC and complete killing within 30 min at concentrations eight times greater than the MIC (See FIG. 10A).

Susceptibility of bacteria grown in biofilm. To further assess the activity of $P_{407}5EC$, bacteria grown as biofilms were tested for susceptibility. Crystal violet staining identified 12 biofilm-forming strains from among 25 strains screened from the test panel. Nine (75%) of the 12 strains showed decreased susceptibility to $P_{407}5EC$, defined as at least a four-fold increase in the MBIC compared to the MIC, when grown as a biofilm (See FIG. 12). The median increase in MBIC compared to the respective MIC of $P_{407}5EC$ for the strains in this set was eight-fold. No evidence of tolerance of biofilm bacteria to $P_{407}5EC$ was observed; the MBEC was the same as the respective MBIC for 10 of the 12 strains.

Susceptibility of bacteria in CF sputum. The 12 biofilm-forming strains were also tested for susceptibility to $P_{407}5EC$ in the presence of CF sputum to model more closely the CF pulmonary microenvironment. The MBCs of $P_{407}5EC$ for all 12 strains, grown under planktonic conditions, increased in the presence of 43% sputum (the highest sputum concentration achievable in the microtiter assay) compared to the respective MBCs under standard conditions (See FIG. 12). Nevertheless, all strains remained susceptible to $P_{407}5EC$ in the presence of sputum. CF sputum inhibited the activity of $P_{407}5EC$ against planktonic bacteria in a concentration dependent manner (See FIG. 10B).

EXAMPLE 4

Nanoemulsion Killing of Individual and Mixed Bacterial Biofilms

A composition comprising nanoemulsion $P_{407}5EC$, 7% saline and 20 mM EDTA was tested for its ability to kill bacteria present in biofilms (individual or mixed).

Biofilm Growth. Bacterial biofilms on polycarbonate membranes were formed following the procedure described in Current Protocols in Microbiology (John Wiley & Sons, Inc., NJ, USA). Polycarbonate membranes were sterilized by exposing the membrane to UV light for 10 minutes each side using sterile forceps or by steam sterilization at 121° C. for 20 minutes. The sterile membrane was placed on the surface of an agar medium with the shiny surface facing upwards. Overnight culture of the bacterial strain of interest was diluted with broth media to an $OD_{600}$ of 0.05 and 0.5 μl of the diluted culture placed onto the shiny surface of the polycarbonate membrane on the agar plate medium. The plate with the membrane was incubated at 37° C. for 24 hours following which; the membrane is transferred to a new agar medium for another 24 hours for biofilm formation.

Bactericidal Assay for Biofilm Bacteria. Polycarbonate membrane with the biofilm was immersed in 250 μl of 20% $P_{407}5EC$ with 20 mM EDTA and 7% sodium chloride (NaCl) in a 1.5 ml eppendorf tube for 3 hours at 37° C. Seven percent NaCl served as the negative control. Following incubation, the membrane was transferred to 15 ml sterile polypropylene tubes containing 10 ml of sterile PBS. One ml of sterile PBS was added to the eppendorf reaction tubes, vortexed and spun at 3500 rpm for 15 minutes. Following centrifugation, the supernatant containing the NE was removed and the bacterial pellet resuspended in their respective 15 ml tube in which the polycarbonate membrane was collected. The 15 ml tube was then vortexed at maximum speed for 3 minutes to get bacteria from membrane into the PBS. One hundred microliters of undiluted and diluted treated and control samples were plated onto LB agar plates for colony count.

Figure 13:
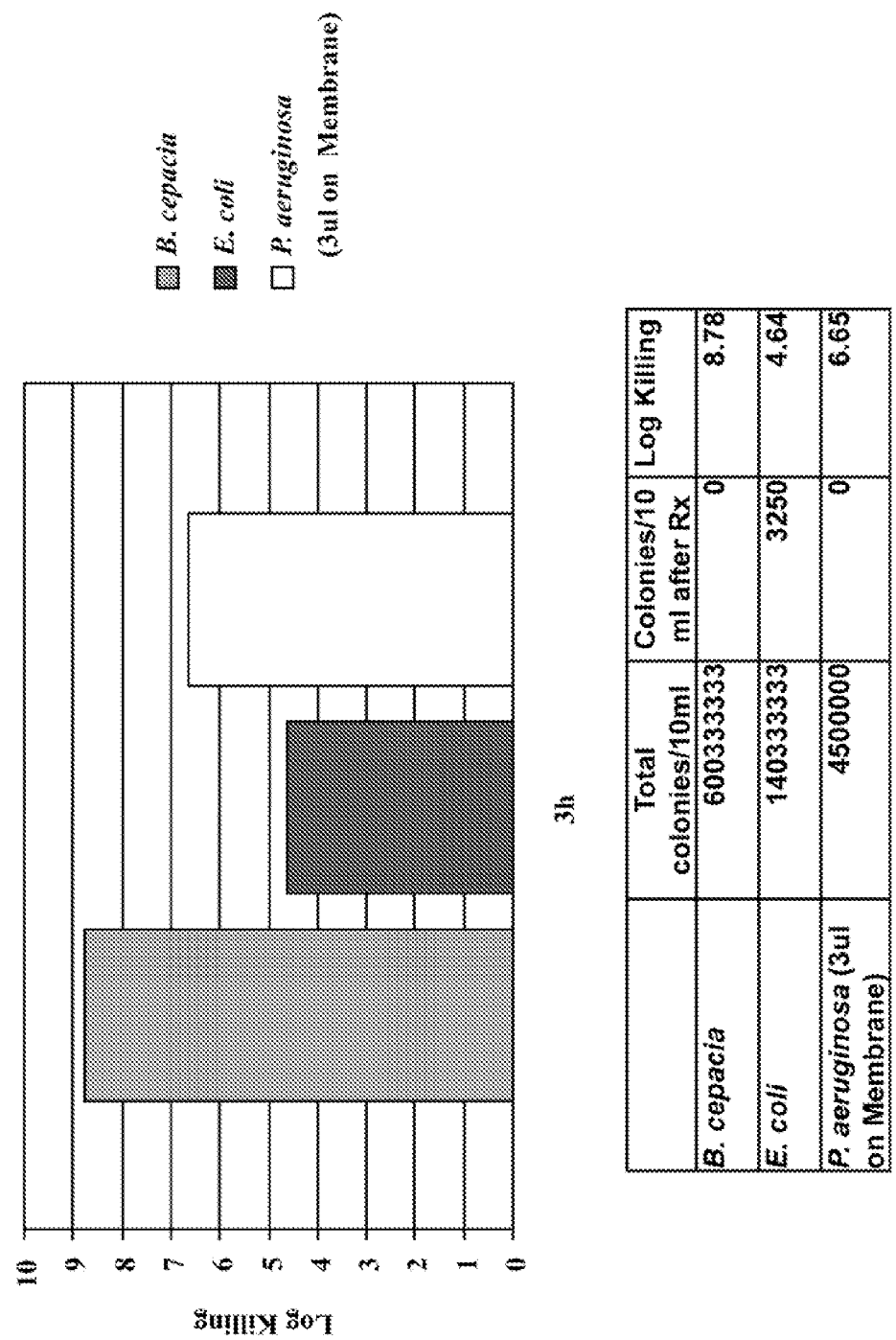
Figure 14:
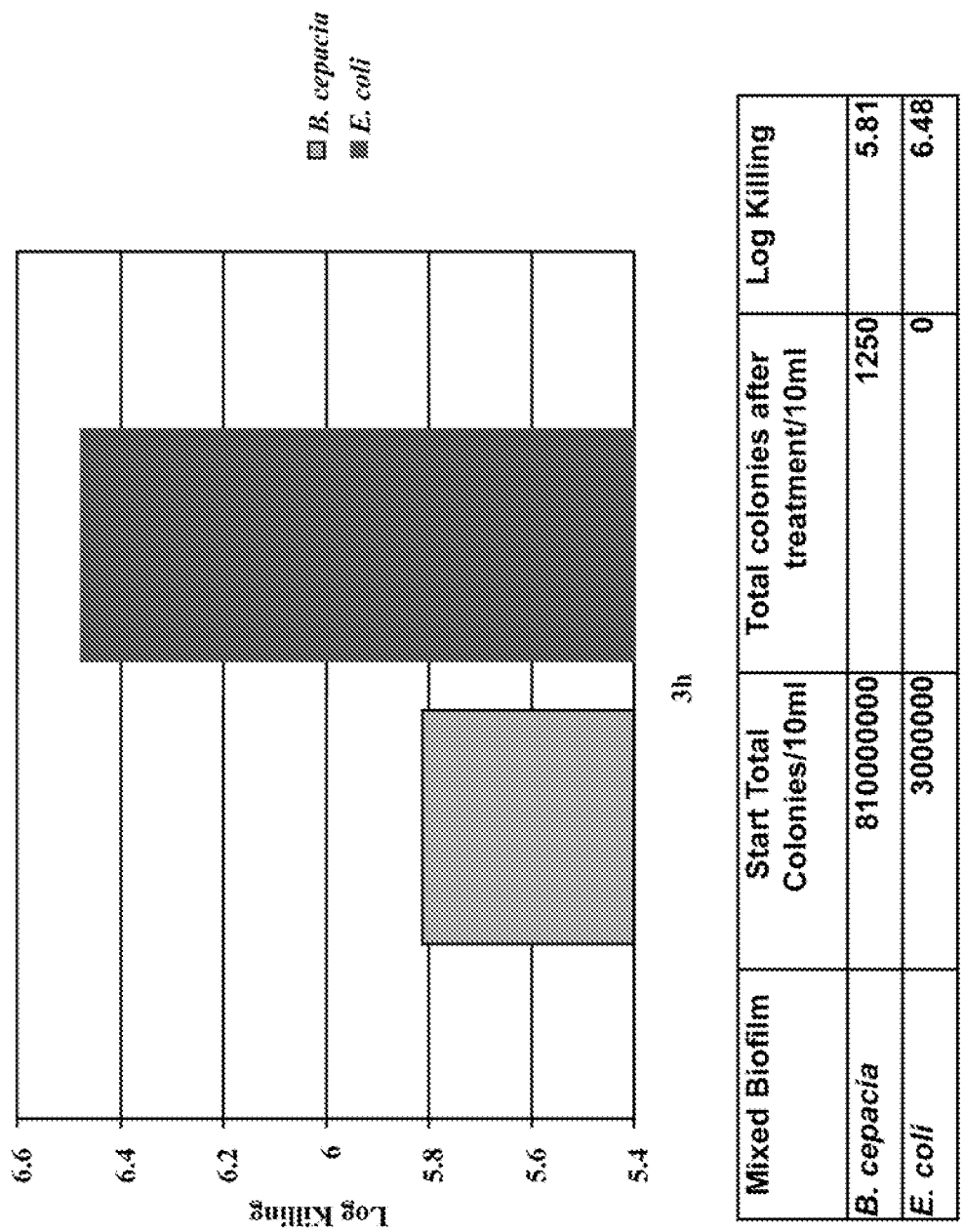
Figure 15:
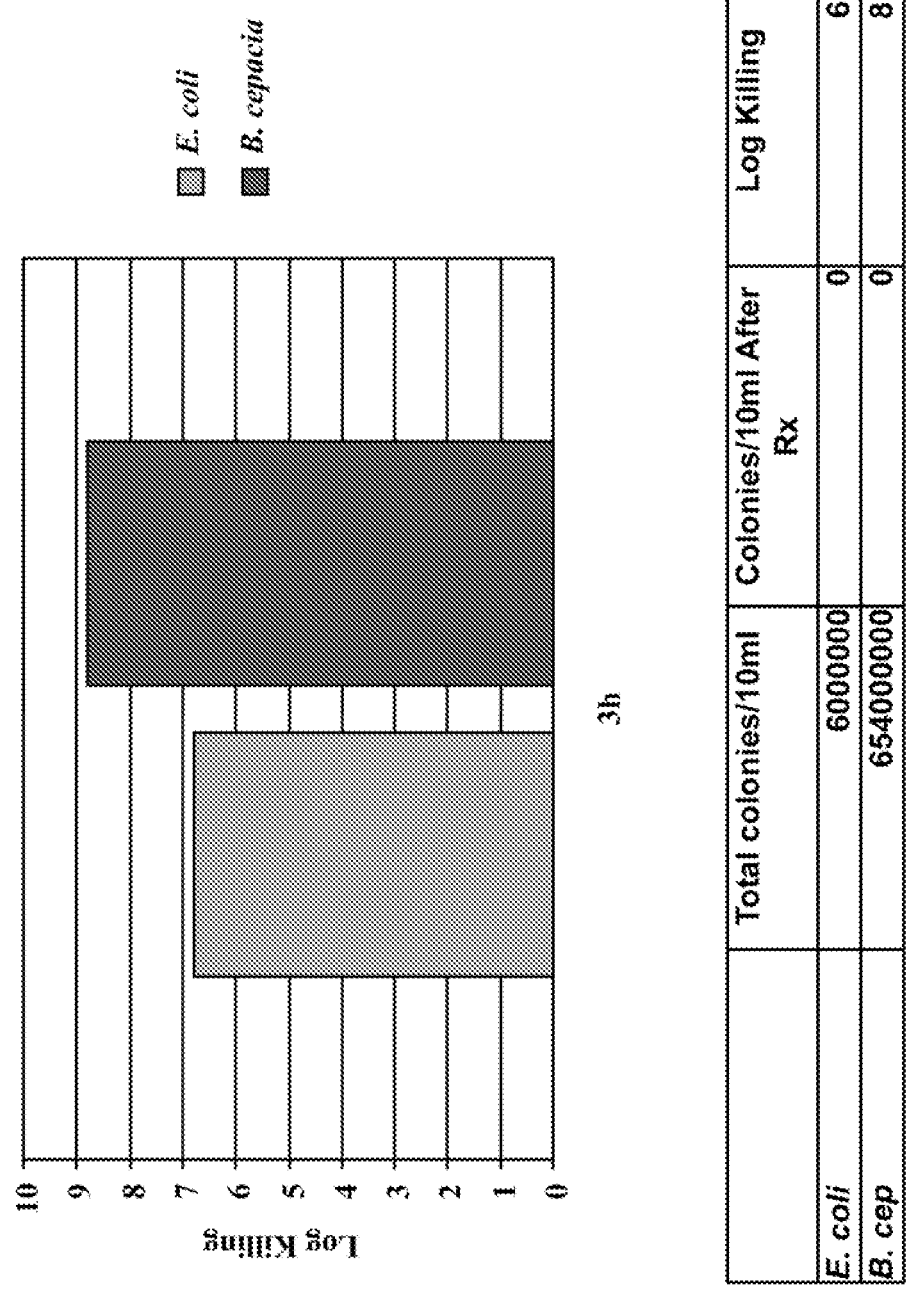
Figure 16:
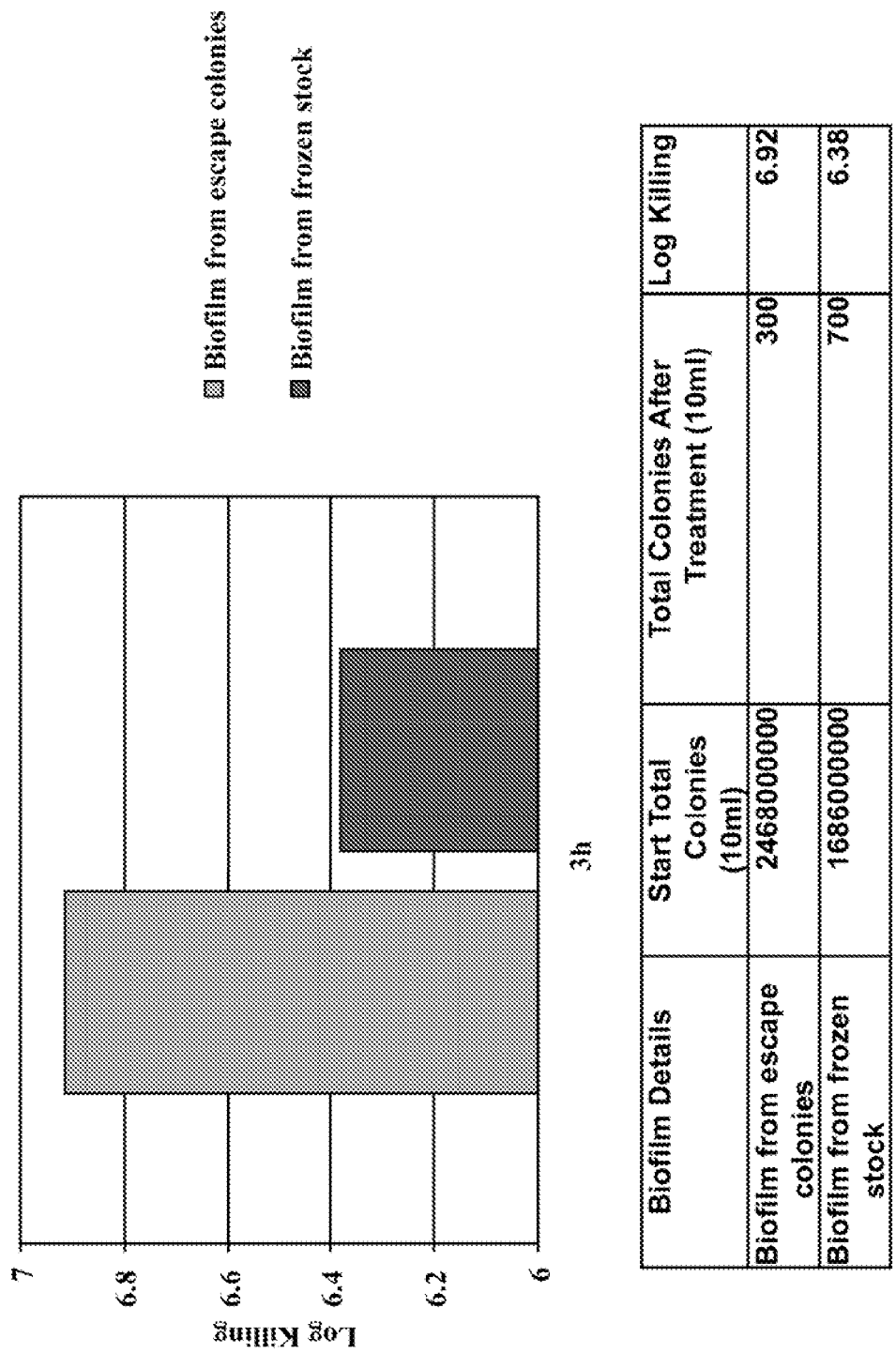

As shown in FIGS. 13-16, 20% $P_{407}5EC$ with 7% saline and 20 mM EDTA was effective to kill bacteria present in biofilms comprising a single bacterial strain (See, e.g., FIG. 13, biofilms comprising a plurality of bacterial strains (See, e.g., FIGS. 14-15), as well as biofilms generated from bacteria that escaped killing in a first round of treatment (See, e.g., FIG. 16), attaining between a 4 to 9 log reduction in bacterial numbers.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of killing and/or inhibiting growth of bacteria within a biofilm comprising:
    A) providing:
        i) a biofilm comprising bacteria; and
        ii) a composition comprising:
            a) a nanoemulsion; wherein said nanoemulsion comprises:
                1) about 3 vol. % to about 15 vol. % of a Poloxamer;
                2) about 3 vol. % to about 15 vol. % of an organic solvent;
                3) about 0.5 vol. % to about 1 vol. % of a halogen-containing compound;
                4) about 3 vol. % to about 90 vol. % of an oil; and
                5) about 5 vol. % to about 60 vol. % of water;
            b) ethylenediaminetetraacetic acid (EDTA); and
            c) a hypertonic salt solution; and
    B) exposing said biofilm comprising bacteria to said composition under conditions such that said composition kills and/or inhibits growth of said bacteria within said biofilm.

2. The method of claim 1, wherein said hypertonic salt solution is a 7% sodium chloride solution.

3. The method of claim 1, wherein said composition comprises 10 mM -20 mM EDTA.

4. The method of claim 3, wherein said composition comprises 20 mM EDTA.

5. The method of claim 1, wherein said nanoemulsion comprises droplets having an average diameter of about 400 nanometers (nm).

6. The method of claim 1, wherein said nanoemulsion is administered via pulmonary administration.

7. The method of claim 6, wherein a nebulizer is utilized for said pulmonary administration.

8. The method of claim 1, wherein said nanoemulsion is co-administered with an antimicrobial agent.

9. The method of claim 1, wherein said composition comprises 20% nanoemulsion.

10. The method of claim 1, wherein said biofilm comprising bacteria resides within the pulmonary system of a subject.

11. The method of claim 10, wherein said subject displays signs and/or symptoms of a respiratory infection.

12. The method of claim 1, wherein said biofilm comprising bacteria resides on and/or within a subject with cystic fibrosis.

13. The method of claim 1, wherein said bacteria are selected from the group consisting of *Burkholderia cepacia* and *Pseudomonas aeruginosa*.

14. The method of claim 1, wherein said bacteria is an *Acinetobacter* species.

15. The method of claim 1, wherein said bacteria is selected from the group consisting of a *Burkholderia multivorans, B. cenocepacia, B. stabilis, B. vietnamiensis, B. dolosa, B. ambifaria, B. anthina, B. pyrrocinia, B. gladioli, Achromobacter xylosoxidans, Stenotrophomonas maltophilia, Pandoraea apista, Pandoraea pnomenusa, Pandoraea pulmonicola, Pandoraea norimburgensis, Pandoraea sputorum, Ralstonia mannitolilytica, Ralstonia pickettii, Staphylococcus aureus, Streptococcus pneumonia, Moraxella, M tuberculosis, Klebsiella, Haemophilus influenzae* and *Staphylococcus epidermidis*.

16. The method of claim 1, wherein said nanoemulsion comprises:
    a) about 3 vol. % to about 15 vol. % of a Poloxamer selected from the group consisting of Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182;
    b) about 3 vol. % to about 15 vol. % of an organic solvent selected from the group consisting of dialkyl-phosphates, trialkyl phosphates, tri-n-butyl phosphate, methanol, ethanol, propanol and octanol, and mixtures thereof;
    c) about 0.5 vol. % to about 1 vol. % of a halogen-containing compound selected from the group consisting of cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides;
    d) about 3 vol. % to about 90 vol. % of an oil selected from the group consisting of plant oils, soybean oil, avocado oil, flaxseed oil, coconut oil, cottonseed oil, squalene oil, olive oil, canola oil, corn oil, rapeseed oil, safflower oil, sunflower oil, animal oils, fish oil, flavor oils, pine oil, Olestra oil, water insoluble vitamins, mineral oils, motor oils, butter, and mixtures thereof; and
    e) about 5 vol. % to about 60 vol. % of water.

17. The method of claim 1, wherein said nanoemulsion comprises:
    a) about 3 vol. % to about 15 vol. % of Poloxamer 407;
    b) about 3 vol. % to about 15 vol. % of ethanol;
    c) about 0.5 vol. % to about 1 vol. % of cetylpyridinium chloride (CPC);
    d) about 3 vol. % to about 90 vol. % of soybean oil; and
    e) about 5 vol. % to about 60 vol. % of water.

18. The method of claim 1, wherein said nanoemulsion comprises:
    a) about 5 vol. % of Poloxamer 407;
    b) about 8 vol. % of ethanol;
    c) about 1 vol. % of cetylpyridinium chloride (CPC);
    d) about 64 vol. % of soybean oil; and
    e) about 22 vol. % of water.

19. The method of claim 1, wherein said bacteria are antibiotic resistant.

20. The method of claim 1, wherein said bacteria are resistant to one or more antibiotics selected from the group consisting of a lactam antibiotic, an aminoglycoside antibiotic, and a quinolone antibiotic.

21. The method of claim 1, wherein said bacteria are resistant to two or more antibiotics selected from the group consisting of a lactam antibiotic, an aminoglycoside antibiotic, and a quinolone antibiotic.

22. The method of claim 16, wherein said cetylpyridinium halide is cetylpyridinium chloride.

23. The method of claim 1, wherein said biofilm comprising bacteria is present within cystic fibrosis sputum.

* * * * *